United States Patent [19]

Spivey et al.

[11] Patent Number: 5,712,890
[45] Date of Patent: Jan. 27, 1998

[54] FULL BREAST DIGITAL MAMMOGRAPHY DEVICE

[75] Inventors: Brett Spivey, Encinitas; Jean-Marie Tran, San Diego; Lee Morsell, Del Mar; George Houghton, San Diego; Steve Horton, Oceanside; Peter Martin, Encinitas, all of Calif.

[73] Assignee: Thermotrex Corp., San Diego, Calif.

[21] Appl. No.: 622,053

[22] Filed: Mar. 26, 1996

Related U.S. Application Data

[63] Continuation of Ser. No. 344,141, Nov. 23, 1994, abandoned.
[51] Int. Cl.$^6$ .................................................. A61B 6/04
[52] U.S. Cl. .............................................. 378/37; 378/98.2
[58] Field of Search ......................... 378/98.2, 98.3, 378/98.7, 98.11, 98.12, 37, 901; 382/132, 134

[56] References Cited

U.S. PATENT DOCUMENTS

| 4,467,361 | 8/1984 | Ohno et al. | 358/213 |
| 5,123,056 | 6/1992 | Wilson et al. | 378/98.6 |
| 5,340,988 | 8/1994 | Kingsley et al. | 250/370.09 |
| 5,367,155 | 11/1994 | Colditz et al. | 250/214 VT |
| 5,485,500 | 1/1996 | Baba et al. | 378/98.8 |

OTHER PUBLICATIONS

Webster's New World Dictionary, Neufeldt, p. 1202.

*Primary Examiner*—Don Wong
*Attorney, Agent, or Firm*—John R. Ross

[57] ABSTRACT

The invention provides a digital x-ray mammography device capable of imaging a full breast. A movable aperture coupled with a movable x-ray image detector permits x-ray image data to be obtained with respect to partially overlapping x-ray beam paths from an x-ray source passing through a human breast. A digital computer programmed with a stitching algorithm produces a composite image of the breast from the image data obtained with respect to each path. In a preferred embodiment, a Schmidt camera images visible light produced at an x-ray to visible light conversion surface onto a digital detector array to produce an overlapping image pane with respect to each overlapping beam path.

48 Claims, 17 Drawing Sheets

FULL BREAST DIGITAL MAMMOGRAPHY DEVICE

This is a continuation of Ser. No. 08/344,141 filed Nov. 23, 1994 now abandoned.

The present invention relates to x-ray imaging devices and specifically to x-ray mammography devices.

BACKGROUND OF THE INVENTION

Film screen x-ray mammography is currently the most effective imaging technique available for the screening and diagnosis of breast cancer. This imaging technique involves directing a beam of x-rays through the breast onto a phosphor screen which converts each x-ray photon into a large number of visible photons. The visible photons expose a sheet of photographic film placed close to the phosphor thus forming an image of the attenuation of x-rays passing through the breast.

There are several limitations to film-screen mammography. A major limitation is that the film serves the combined purpose of both the image acquisition function and the image display function. In addition, the range of contrast or latitude of the film is too limited to display the entire range of contrast in the female breast. Because of the limited latitude and dual acquisition/display function of film, a film-screen x-ray mammogram is typically overexposed in one area and underexposed in another area due to the thickness and composition variations of the breast across the image. The gray-scale level of x-ray film has a sigmoidal response as a function of exposure which results in difficulties in distinguishing contrast differences at the extremes of the exposure range; that is, in the most radiodense and in the most radiolucent areas of the image. This creates difficulties in detecting and diagnosing soft tissue masses in these areas. This problem is accentuated in women with radiodense breasts, which includes most younger women. Other significant problems of film-screen mammography include the need for significantly increased x-ray dose for women with large dense breasts and, in many cases, the need to repeat images due to sub-optimal exposure settings.

Digital mammography has been proposed as a technology which replaces the phosphor/film detector with a digital image detector, with the prospect of overcoming some of the limitations of film-screen mammography in order to provide higher quality mammographic images. A potential advantage of digital mammography involves the separation of the image acquisition function from the image display function. Digital detectors also provide a much greater range of contrast than film and the contrast response function is linear over the entire range. This would allow digital detectors to more easily distinguish subtle differences in attenuation of x-rays as they pass through soft tissue in the breast. Differences in attenuation due to thickness and composition variations across the breast can be subtracted out of the digital data in the computer and the residual contrast can then be optimized for the particular viewing mechanism, be it film or a computer monitor. The residual contrast differences can then be analyzed to search for soft tissue masses and architectural distortion indicative of malignant cancer. Other advantages of digital mammography include digital image archival and image transmission to remote locations for viewing purposes.

Two recent patents disclose systems which digitally image a small area of the breast in order to facilitate needle placement for needle-core biopsy. In the system manufactured by Lorad Medical Systems and described in U.S. Pat. No. 5,289,320 (issued Feb. 22, 1994 to Pellegrino, et al.), light emitted a phosphor screen is coupled to a CCD array with a commercially available lens system. In a system manufactured by Fisher Imaging Corporation and described in U.S. Pat. No. 5,078,142 (issued Jan. 7, 1992 Siczek, et al.), light emitted from a phosphor screen is coupled to a CCD array with a fiber-optic taper.

At the time of this application, digital image detectors with the required image format, spatial resolution, dynamic range, and quantum efficiency to effectively image the full breast are not commercially available. Various approaches are presently being proposed and investigated to achieve a digitally acquired images of the full breast. For example, Yaffe et. al. (Proc. SPIE, 1989; 1010: 306–313) has proposed a scanned-slot system which uses a time-delay integration similar to that described by Holdsworth et at. (Proc. SPIE, 1990; 1231: 316–326), in which the breast is scanned in continuous manner while data is shifted and integrated in a CCD.

SUMMARY OF THE INVENTION

This invention provides a digital x-ray mammography device capable of imaging a full breast. A movable aperture coupled with a movable x-ray image detector permits x-ray image data to be obtained with respect to partially overlapping x-ray beam paths from an x-ray source passing through a human breast. A digital computer programmed with a stitching algorithm produces a composite image of the breast from the image data obtained with respect to each path. In a preferred embodiment, a Schmidt camera images visible light produced at an x-ray to visible light conversion surface onto a digital detector array to produce an overlapping image pane with respect to each overlapping beam path.

DETAILED DESCRIPTION OF PREFERRED EMBODIMENTS

First Preferred Embodiment

Figure 1:
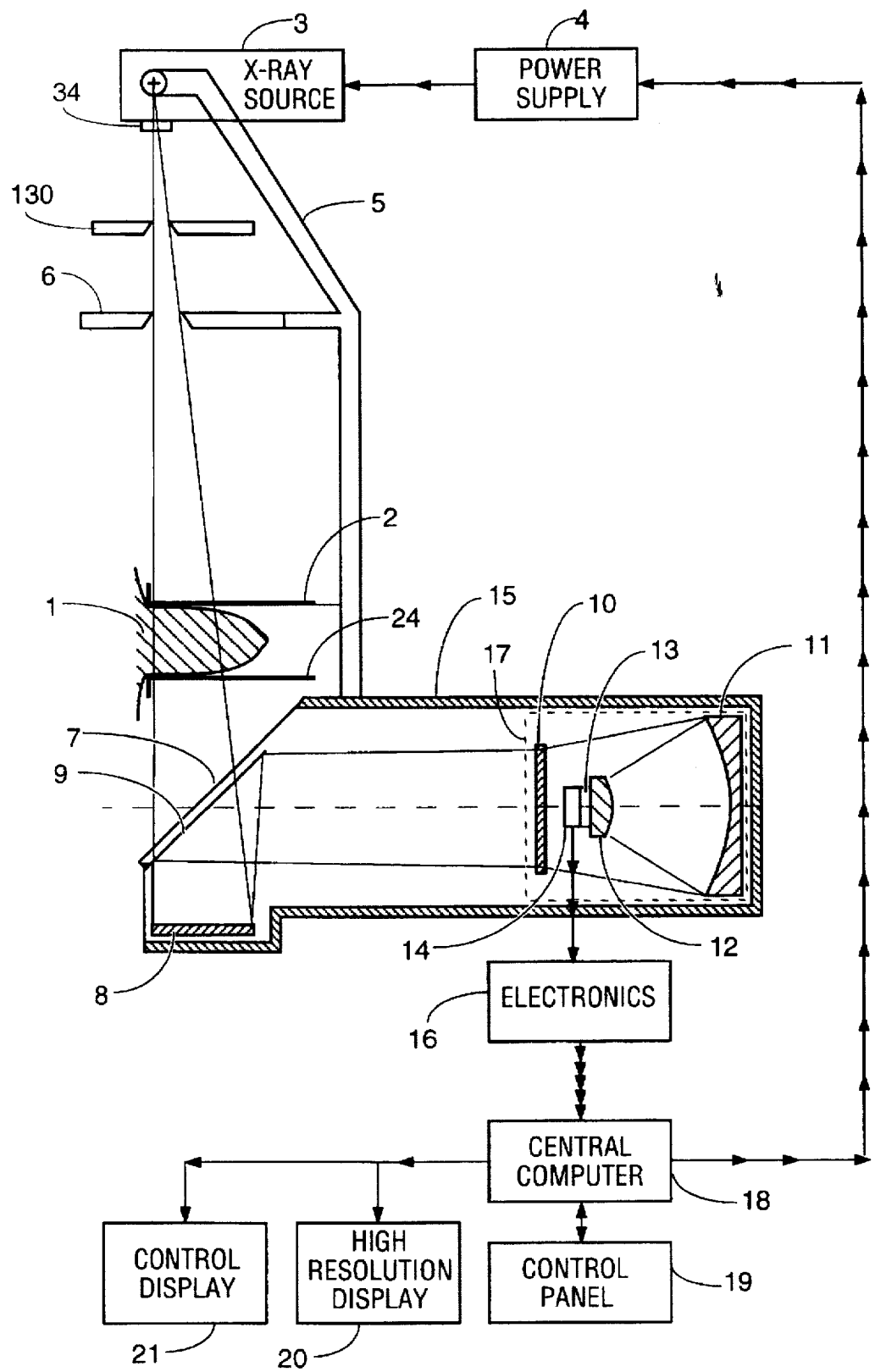
FIG. 1 is a schematic drawing showing the principal elements of a first preferred embodiment of the invention fabricated by inventors and their co-workers.

A schematic of the key elements of a first preferred embodiment of a digital mammography device which has been fabricated and tested by the inventors and their fellow workers is shown in FIG. 1. The primary components of the device consist of an x-ray source 3, a conventional breast compression mechanism 2, and a digital detector system 15.

X-ray source 3 incorporates a standard Model B110/ M149 Varian/Eimac x-ray generation tube with a tungsten anode. High voltage power is applied to the x-ray source 3 with a commercially available high voltage power supply 4. The ideal x-ray source has x-rays emitted from a point source of substantially small areal extent. Our x-ray source emits x-rays from an area typically 300 microns in diameter. An x-ray filter 34 fabricated from a moderate x-ray attenuator such as a 50 micron thick sheet of silver, for example, provides a narrower energy spectrum of x-rays to provide a higher quality x-ray image. This embodiment locates the x-ray tube 3 at 0 elevation, aperture 6 at 32 cm, a breast tray 24 at 64 cm, and a phosphor screen 8 at 87 cm.

The breast 1 is compressed between the breast tray 24 and an adjustable breast compression paddle 2. This immobilizes the breast 1 during x-ray exposure, helps to equilibrate the x-ray exposure across the breast, and reduces the effects of x-ray scatter in the breast.

The digital detector system 15 consists of a phosphor screen 8, pellicle mirror 9, x-ray window 7 which is transparent to x-rays and opaque to visible light, and a Schmidt optical system 17. The entire digital detector assembly 15 is enclosed in a sealed housing to eliminate dust and ambient visible light. The pellicle mirror 9 is comprised of a 9 micron thick sheet of optical grade nitrocellulose stretched over a metal frame. The pellicle mirror 9 has a very thin (approximately 1 micron) layer of aluminum silicate deposited on the its underside. In the preferred embodiment, phosphor material on phosphor screen 8 is a 10.5 cm×7.7 cm sheet of terbium-activated gadolinium oxysulfide (Lanex, by Kodak Corporation). Each x-ray photon striking the phosphor screen 8 is converted into a large number of visible photons. A visible light image of the breast 1 is therefore produced on the phosphor screen 8. X-rays pass with minimal amount of attenuation through the pellicle 9, while the visible light image generated on the phosphor screen 8 is reflected from the underside of the pellicle mirror 9 directly towards the Schmidt optical system 17.

The visible light image is digitally imaged by a Schmidt optical system 17 which consists of a curved primary mirror 11, Schmidt aspheric corrector plate 10, doublet lens 12, and charged coupled device (CCD) array 13. Schmidt cameras are disclosed in Modern Optical Engineering, by Warren Smith, McGraw Hill, N.Y., 1990, pg. 446. These cameras are known for maximum light collection efficiency (the preferred embodiment has f number f/0.83) with a minimum amount of optical aberration.

The preferred embodiment utilizes a commercially available Model KAF-6300 CCD array 13 (supplied by Kodak Corporation) which contains an array of 2048×3072 light sensitive pixels. The dimensions of each pixel are 9 microns×9 microns, resulting in 1.84 cm×2.76 cm imaging area. The Schmidt optical system provides a de-magnification ratio of 6:1 between the phosphor screen 8 and the CCD array 13. The separation distance of 23 cm between the breast tray 24 and the phosphor screen 8 produces a geometrical magnification of 1.35 between the breast tray 24 and the phosphor screen 8. In addition, this separation distance contributes to the reduction of the background signal produced by x-rays scattered by the breast 1. The corresponding pixel size is 54 micron×54 microns at the phosphor 8 and 40 microns×40 microns at the breast tray 24. This results in a 7.7 cm×10.5 cm image at the breast tray 24.

A driver/preamplifier electronics assembly 14 is provided at the CCD array 13, with cables leading to external detector electronics assembly 16 containing analog-to-digital conversion circuitry to convert the analog CCD data into 12-bit digital values at a 5 MHz readout rate. The electronics assembly 14 and the electronic assembly 16 are custom designed and fabricated by our co-workers. Digital data from the CCD array 13 is stored in the computer 18 for display on the high resolution display monitor 20. Control panel 19 used to control the x-ray source is linked to the data acquisition functions through the computer 18. Parameters associated with control panel 19 are displayed on control display 21.

Figure 2:
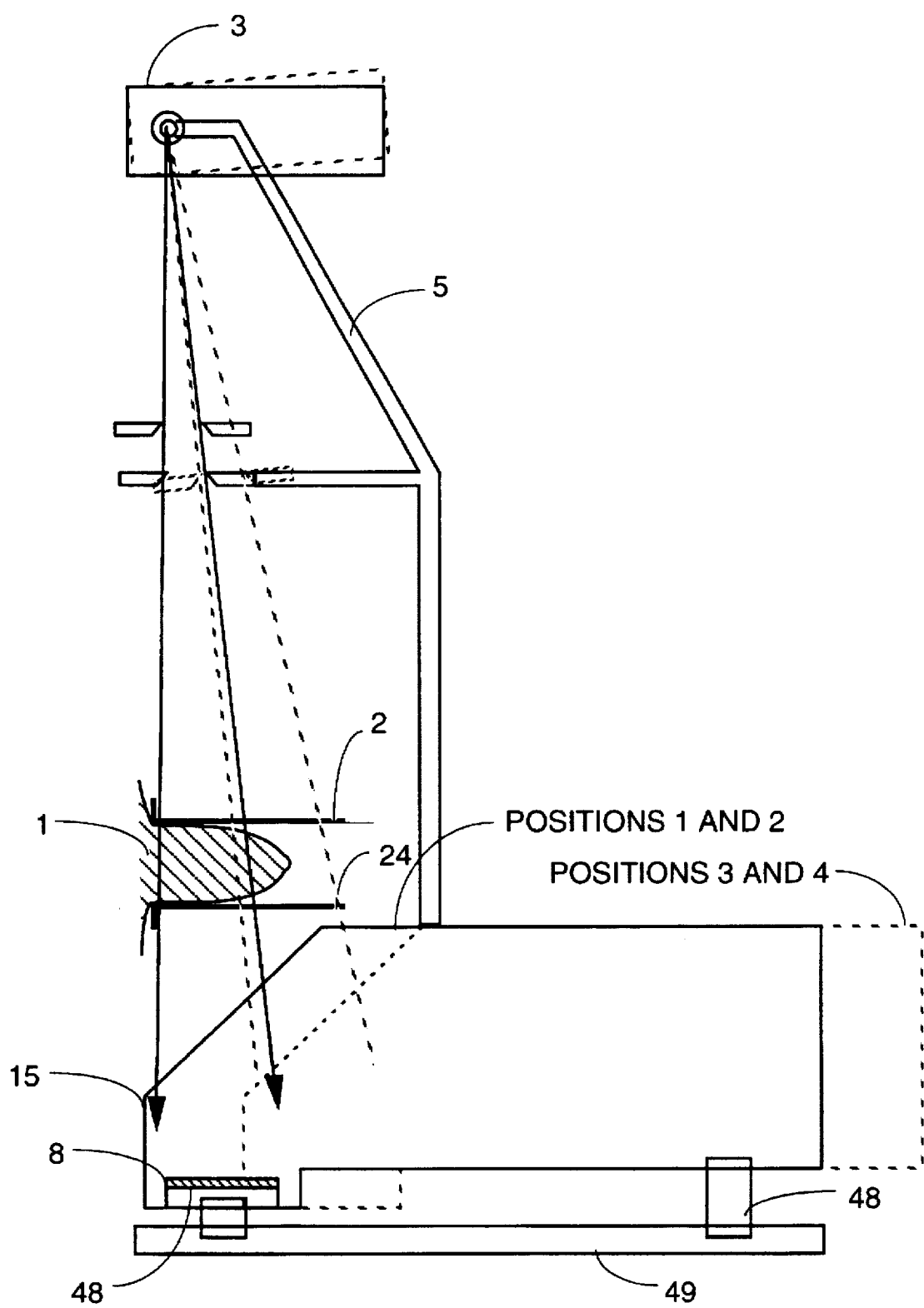
FIG. 2 is a side view of the embodiment showing the different positions of the digital detector assembly.
Figure 3A:
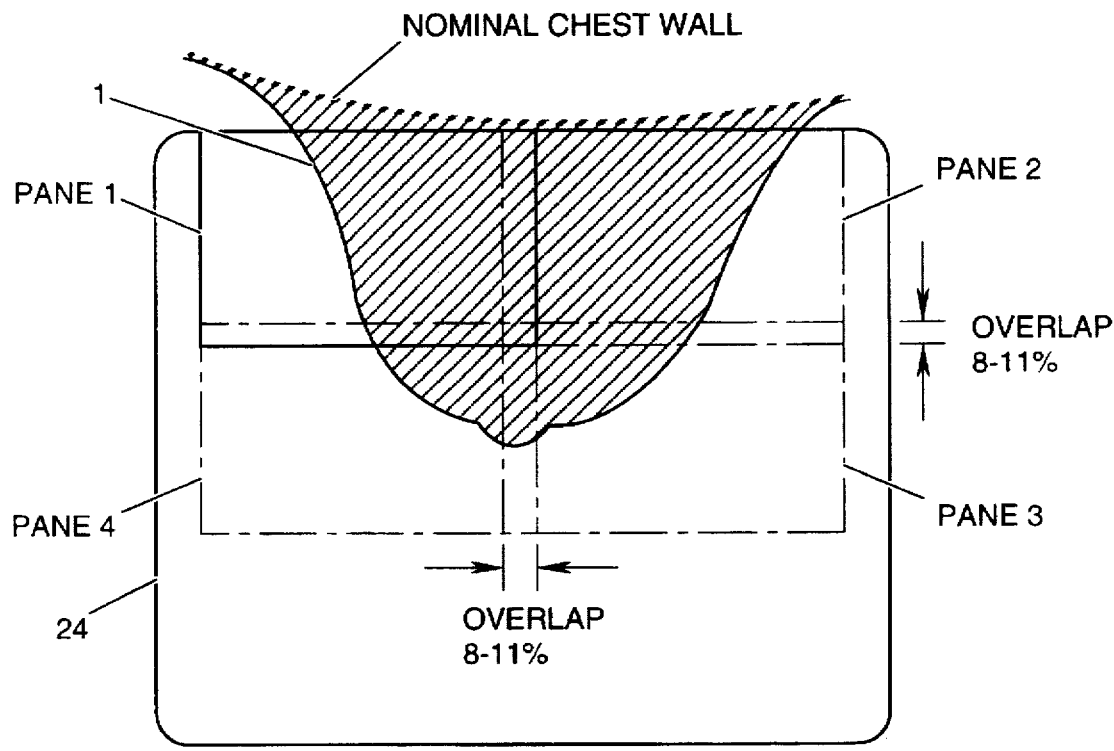
FIG. 3a shows the different image pane positions of the first preferred embodiment of the invention.

The x-ray source 3, aperture 6, and the digital detector assembly 15 move relative to the clamped breast 1 to sequentially image four individual sections or quadrants of the breast 1 as shown in FIG. 3a. The quadrants overlap by approximately 10% resulting in a final composite image which is 20.5 cm×15 cm. FIG. 2 shows a side view of the different positions of the detector assembly 15. Motion of detector assembly 15 is parallel to the breast tray 24 utilizing a pair of LM Corporation Type HK ball slides 48 mounted on HK Corporation rails 49 which are in turn mounted on the frame (not shown) of the mammography unit. Motion control is accomplished with American Precision Industries stepper motors, 37488 power supplies, and B341-01 brakes, and Warner R0505 ball screw assemblies (not shown). A mechanical linkage system 5 sequentially positions the x-ray source 3 as the position of detector assembly 15 changes. Aperture 6 is sequentially positioned with respect to the detector assembly 15 and the x-ray source 3 by the linkage system 5 in order to confine the x-ray energy within the area defined by the phosphor 8.

Figure 3B:
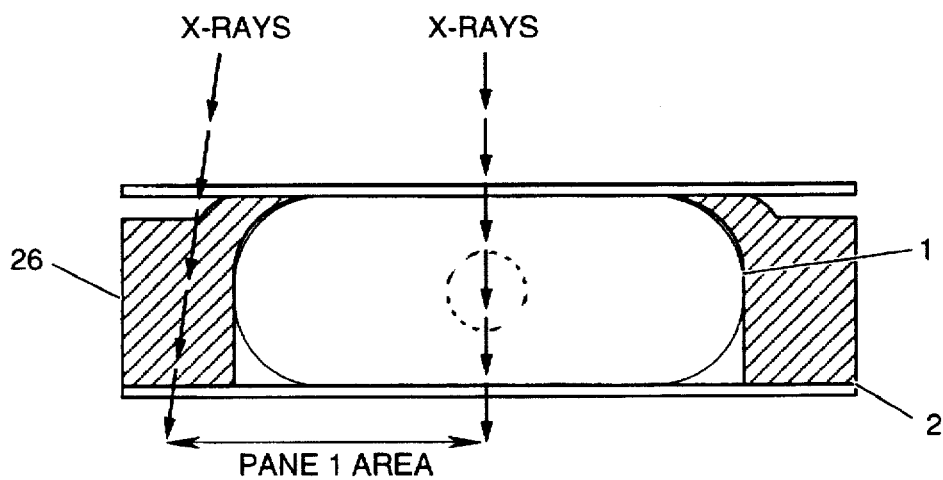
FIG. 3b shows the placement of x-ray attenuating material surrounding the breast.

FIG. 3a demonstrates that a typical breast does not cover the entire area comprised of the individual image panes 1 through 4. The approximately 100 to 1 variation in x-ray intensity between the non-breast and breast regions results in two problems. The predominant problem involves excessive conversion of x-rays to visible light in the non-breast region of the phosphor 8 which results in scatter of some of this visible light from the surfaces and edges of components in the Schmidt optical system 17. This scattered visible light commonly known as "veiling glare" contributes to spatially dependent noise in the breast images. In addition, "blooming" or overexposure of the pixels in the CCD 13 which are in the non-breast region and close to the breast results in a spillover of electric charge into the neighboring pixels. These problems are alleviated in the first preferred embodiment by the placement of an x-ray attenuating material 26 in the areas around the breast as shown in FIG. 3b. The preferred embodiment uses a bolus material commonly used for radiation therapy which is marketed under the name "Supertab". This material approximates the x-ray attenuation of the breast and adjusts the intensity of the x-rays passing through the non-breast region to an acceptable level.

Figure 4A:
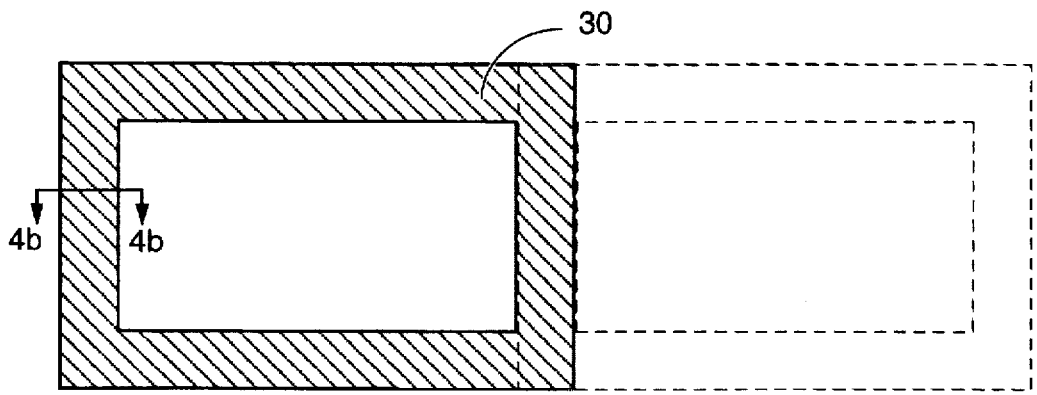
FIG. 4a shows two positions of a variable thickness x-ray apodizer.
Figure 4B:
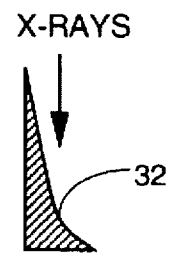
FIG. 4b shows the thickness dimension of the x-ray apodizer.
Figure 4C:
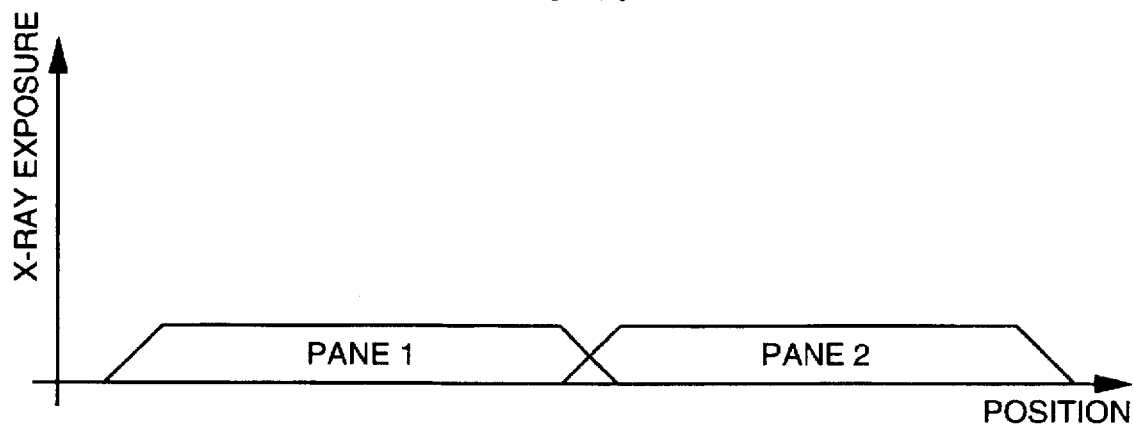
FIG. 4c shows the spatial distribution of x-ray exposure for each of two image panes.

X-ray dose limitations to the patient are a primary concern for a screening procedure such as mammography. The x-ray exposure level for each of the four image panes do not exceed the allowable exposure levels. However, because the image panes overlap slightly, the exposure levels in the overlap regions can exceed the average exposures by a factor of two, and a factor of four in the case of the region where the four panes overlap. We have developed an apodizer technique for reducing the exposure level specifically in the overlap region for each of the four image panes in order to reduce the total exposure in the overlap to an acceptable level. FIG. 4a–c illustrates an apodizer we have fabricated and implemented in our invention. The apodizer is placed at the aperture 6 as shown in FIG. 1. The preferred embodiment uses a variable thickness x-ray attenuator 30, fabricated from aluminum which is a moderate attenuator of x-rays, which is fabricated in the shape which resembles a picture frame. The outer dimensions of the variable attenuator 30 are 4.8 cm×6.3 cm so that the shadow cast by x-rays passing through this apodizer line up with the edges of each image pane. The inner dimensions of the attenuator 30 are 10% smaller than the outer dimensions and the thickness dimension 32 is shaped so that the attenuation of x-rays passing through the attenuator 30 increases linearly as one moves away from the inner dimension of the attenuator. Attenuator 30 is surrounded by a separate attenuator of 0.5 cm thickness of lead which substantially attenuates x-rays in the periphery. The resultant x-ray exposure per image pane falls off linearly in the overlap region as shown in FIG. 4c. Attenuator 30 is centered with respect to each image pane before each x-ray exposure by moving the aperture 6 with the linkage system 5. FIG. 4b demonstrates that the total exposure in the overlap region between two image panes which is a sum of exposures of the individual image panes is reduced to the average exposure level of each image pane, except where the four panes overlap in which the exposure is reduced to twice the average exposure level of each image pane.

Data Acquistion

The breast 1 is positioned between breast tray 24 and breast compression paddle 2. Bolus material 26 is positioned around the breast 1 as shown in FIG. 3b. The x-ray exposure level is predetermined from exposure level charts dependent on breast size and composition. X-ray exposure is determined by a combination of x-ray tube voltage and current, and x-ray exposure time. Each image pane 1 through 4, shown in FIG. 3a, is sequentially imaged. Typical x-ray exposure times are 1 second per image pane and approximately 1 second is required to move the detector assembly from image pane to image pane. Therefore, approximately 8 seconds are required to image the full breast. For each image pane, the x-ray beam passes through the aperture 6, breast paddle 2, breast 1, x-ray window 7, pellicle mirror 9, and strikes the phosphor screen 8. Visible light from the phosphor screen 8 is collected on the CCD array 13 by Schmidt optical system 17. Digital data from the CCD array 13 is readout by the electronics assembly 16 while the detector assembly is moving to the next image pane.

The CCD camera output data is in a 1024×1024 pixel array. The value of the luminance from the CCD camera has a resolution of 12 bits or 4096 luminance values. These four image panes are stored in the computer as $I^{raw}_m(x_i,y_j)$ (i,j=1,N) (m=1,4) where N=1024.

Combining of Image Panes

Our device produces four digital x-ray images panes which overlap by approximately 10%. As shown in FIG. 3a, the area of these four image panes contain a breast and surrounding areas outside the breast. We describe here a computer processing procedure which we call "stitching" which identifies identical features in the overlap areas of the image panes and uses this information to register the panes in order to form a single seamless image of the full breast. We implement the stitching procedure by the following five steps; 1) characterization and calibration of system, 2) preprocessing of the four image panes, 3) distortion correction of each image pane, 4) correlation analysis of at least a subsection of each overlap region to determine the vertical and horizontal offsets of each pane relative to the neighboring panes, 5) registration of the four image panes on a single grid using the offset information, and 6) adjustment the pixel values in the overlap areas (blending) in order to provide a seamless image.

1) Characterization and Calibration of System

The digital mammography device is initially characterized in order to identify hardware imperfections in the x-ray source 3, phosphor screen 8, Schmidt optical system 17, and CCD array 13. These hardware imperfections include dead or weakly responding pixels in the CCD, electronic noise in the CCD array, spatial imperfections in the phosphor, spatially varying illumination of the x-ray source, gain variations of the pixels in the CCD array, distortions introduced by the optical system 17, and rotations of the detector assembly 15 as it moves to the four image pane positions. The characterization information of the hardware imperfections is used to preprocess the breast images produced by the mammography device in order to improve the registration of the four image panes to produce a seamless image and to maximize the final image quality.

The optical center of the Schmidt optical system 17 is determined as part of the assembly procedure of the optical system 17. CCD array 13 is bonded to the doublet lens 12 to be reasonably symmetric with respect to this optical center. Finally, the pixel location corresponding to the optical center is determined and stored in the computer 18 as a two dimensional pixel location OC. For the preferred 1024×1024 CCD array 13, the optical center OC should be reasonably close to the pixel location (512,512).

The characterization procedure requires the acquisition of eight dark field images and eight white field images for each of the four image pane positions shown in FIG. 3a. Dark field images are acquired with the x-ray source 3 turned off in order to characterize the electronic noise in the system. White field images are acquired by placing a 2 cm thick sheet of lucite on the breast tray 24 and illuminating the phosphor 8 with x-ray source 3 in order to characterize the spatially varying illumination of the x-ray source 3.

We subtract a dark field frame from a white field frame to produce a residual frame and average eight of these residual frames together to form one calibration frame per image pane. Small imperfections in the phosphor 8, and dead or weak pixels in the CCD array 13, defined as having greater than 15% variation in luminance, are identified as defective pixels in the calibration frame Defective pixels are corrected in the calibration frames by interpolation of eight nearest neighbors for point defects and six nearest neighbors for column or row defects. These four calibration frames (one for each pane position) are then stored in the computer 18 as $I^{cal}_m(x_i,y_j)$ (i,j=1,N) (m=1,4) and the positions of each defective pixel are stored as a defect map. We also average the six million pixel values in the each of the four calibration frames and store this information as $MEAN_m$ (m=1,4). A single dark field image is stored as $I^{dark}_m(x_i,y_j)$ (i,j=1,N) (m=1,4).

Figure 5:
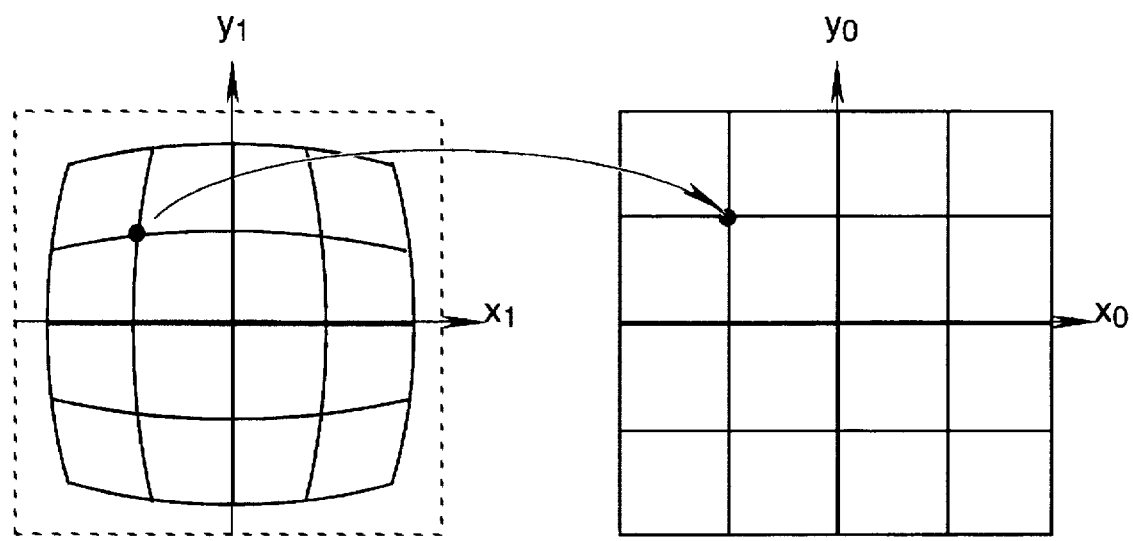
FIG. 5 illustrates distortion correction of barrel distortion for an image pane.

Image distortions complicate the registration of the four image panes and are visible in the final image. These image distortions include pincushion or barrel distortion due to the Schmidt optical system 17 and distortions due to the imaging geometry such as relative rotation of the individual image panes arising from the postion changes of the digital detector assembly 15. An example of barrel distortion is shown in FIG. 5. The stitching algorithm characterizes the image distortions and uses this information to correct each breast image pane. The characterization is accomplished with a 24 cm×18 cm calibration grid comprised of a two-dimensional array of 1 mm diameter copper dots spaced 0.5 cm apart on a standard electical circuit board. The calibration grid is placed on the breast tray 24 so as to fully cover all of the four pane positions. An x-ray image is acquired at each of the four image pane positions.

For each image pane, the pixel coordinates $(x_i, y_j)$ (i,j=1,N) of the calibration grid can be related to observed distorted pixel coordinates $(X_i,Y_j)$ (i,j=1,N) obseved by the CCD array 13. The preferred embodiment uses a third-order polynomial mapping $$X_i = a_0 + a_1x_i + a_2y_i + a_3x_i^2 + a_4x_iy_i + a_5y_i^2 + a_6y_i^3 + a_7x_iy_i^2 + a_8x_i^2y_i^2 + a_9y_i^3 \quad (1)$$

$$Y_i = b_0 + b_1x_i + b_2y_i + b_3x_i^2 + b_4x_iy_i + b_5y_i^2 + b_6y_i^3 + b_7x_iy_i^2 + b_8x_i^2y_i^2 + b_9y_i^3$$

where $a_n$ (n=0,1,2, . . . ,9) and $b_m$ (m=0,1,2, . . . ,9) are the distortion calibration constants. Reasonable accuracy can be achieved with a third-order polynomial fit in $(x_i, y_j)$ as displayed in equation (1), although higher accuracy can be achieved by including more orders in the polynomial fit. The distortion calibration constants $a_j$ (i=1,2, . . . ,9) and $b_j$ (i=1,2, . . . ,9) depend on the image distortion produced by the Schmidt optical system 17, distortions and rotations introduced by moving the digital detector assembly 15 to the four pane positions, and also the overall position and rotation of the calibration grid with respect to the CCD pixel array when the calibration grid is placed on the breast tray 24. A rotation angle for each image pane is extracted from equations (1) and the overall rotation angle of the calibration grid is obtained by summing the rotation angles of the four image panes and dividing by four. This overall rotation angle is removed from the measured data $(X_i,Y_j)$. The distortion constants $a_n$(n=0,,2, . . . ,9) and $b_m$ (m=0, 1,2, . . . ,9) are derived with respect to the independently measured optical center OC of the Schmidt camera assembly 17. Separate sets of distortion constants are derived for each of the four image pane positions. These distortion constants calculated to subpixel accuracy using a standard least-squares procedure which is described in detail in Section 3.6 (pg.61-75) of "Digital Image Warping", by George Wolberg, IEEE Computer Society Press, Los Alamitos, 1990. The distortion constants $a_n$ (n=0, 1,2, . . . ,9) and $b_m$ (m=0,1,2, . . . ,9) for each of the four image panes (72 values) are stored in the computer 18.

2) Preprocessing of Images

We acquire four images panes of the breast called $I^{raw}_m(x_i,y_j)$ (i,j=1,N) (m=1,4) as discussed in the data acquisition section. Dead pixels in each image, identified by the defect map, are corrected by the interpolation procedure discussed in the calibration section. The images are then corrected for gain variations of the CCD pixels and spatial variations of the x-ray source by a procedure commonly known as "flat fielding", $$I^{cor}_m(x_i,y_j)=[I^{raw}_m(x_i,y_j)-I^{dark}_m(x_i,y_j)]*MEAN_m/I^{cal}_m(x_i,y_j) \quad (2)$$

In equation (2), $I^{cor}_m(x_i,y_j)$ (i,j=1,N) (m=1,4) are the corrected image panes which are stored in the computer 18. * denotes a scalar multiplication, and / denotes a pixel-by-pixel division.

The flat fielding procedure also corrects for the spatially varying x-ray exposure of each image pane in the overlap region. The luminance values in the overlap regions of the raw images $I^{raw}_m(x_i,y_j)$ fall off linearly from as one approaches the edge of each image pane due to the variable attenuator 30. From equation (2), the flat fielding procedure automatically adjusts the luminance values in the overlap regions to produce an image $I^{cor}_m(x_i,y_j)$ of each image pane which appears to be taken with no variable attenuator 30 in place. The flat fielding procedure effectively removes the effects of the variable attenuator 30 by adjusting the luminance values of the pixels in the overlap regions to appear that if the breast 1 were removed these pixels would each receive an equivalent amount of x-ray photons.

Due to slight variations in the total x-ray exposure per image pane, the four image panes exhibit an average luminance which varies from image pane to image pane. To correct for this effect for image pane 1 and image pane 2, we first calculate average luminance values $G_1$ and $G_2$ in the overlap region of $I^{cor}_1(x_i,y_j)$ and $I^{cor}_2(x_i,y_j)$, respectively, by summing the luminarice values of the pixels in the overlap region of each respective image pane and then dividing by the number of pixels in the overlap region. We then normalize image pane 2 to image pane 1 by calculating $$I^{norm}_2(x_i,y_j)=[G_1/G_2]*I^{cor}_2(x_i,y_j) \quad (3)$$

We repeat this procedure by normalizing image pane 3 to image pane 2 and then image pane 4 to image pane 3 so that all four image panes appear to have been acquired with the same total x-ray exposure per image pane.

3) Distortion Correction of Images

Each image $I^{norm}_m(x_i,y_j)$ is corrected for distortions and relative rotation by mapping the distorted image $I^{norm}_m(x_i, y_j)$ onto a regular grid using the distortion constants $a_n$(n= 1,2, . . . ,9) and $b_m$ (m=1,2, . . . ,9) and the optical center location OC stored in the computer 18. The distortion correction, shown graphically in FIG. 5 for the case of barrel distortion, is accomplished such that the location of the optical center OC remains fixed. The distortion correction also rotates each image pane such that the axes of each image pane are parallel to each other. The location of each distortion corrected pixel location generally falls between the regularly spaced pixel locations. We utilize a bilinear interpolation in order to remap each corrected point to a point on the regular grid. This procedure is discussed in detail in Section 3.5.1 (pg. 58–61) of "Digital Image Warping", by George Wolberg, IEEE Computer Society Press, Los Alamitos, 1990. Higher accuracy can be achieved by using a higher-order Lagrange polynomial interpolation as discussed in Section 3.6 of the same text. The distortion corrected images for each image pane 1 through 4 are stored in the computer 18 as $I_1(x_i, y_j)$, $I_2(x_i, y_j)$, $I_3(x_i, y_j)$, and $I_4(x_i, y_j)$ (i,j=1,N). Each image $I_m(x_i, y_j)$ is an N×N matrix of 12-bit digital values.

4) Determination of Relative Offsets

Figure 6A:
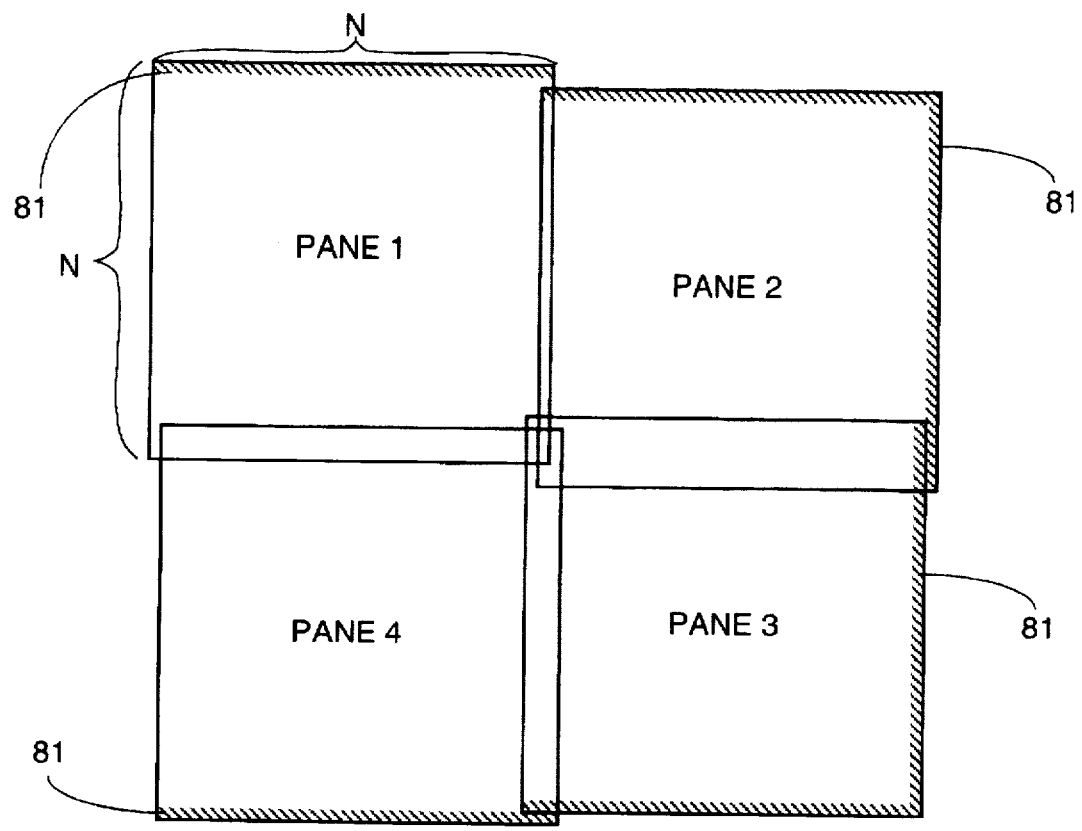
FIG. 6a and 6b illustrate the registration of the four distortion corrected image panes onto a single full grid.
Figure 6B:
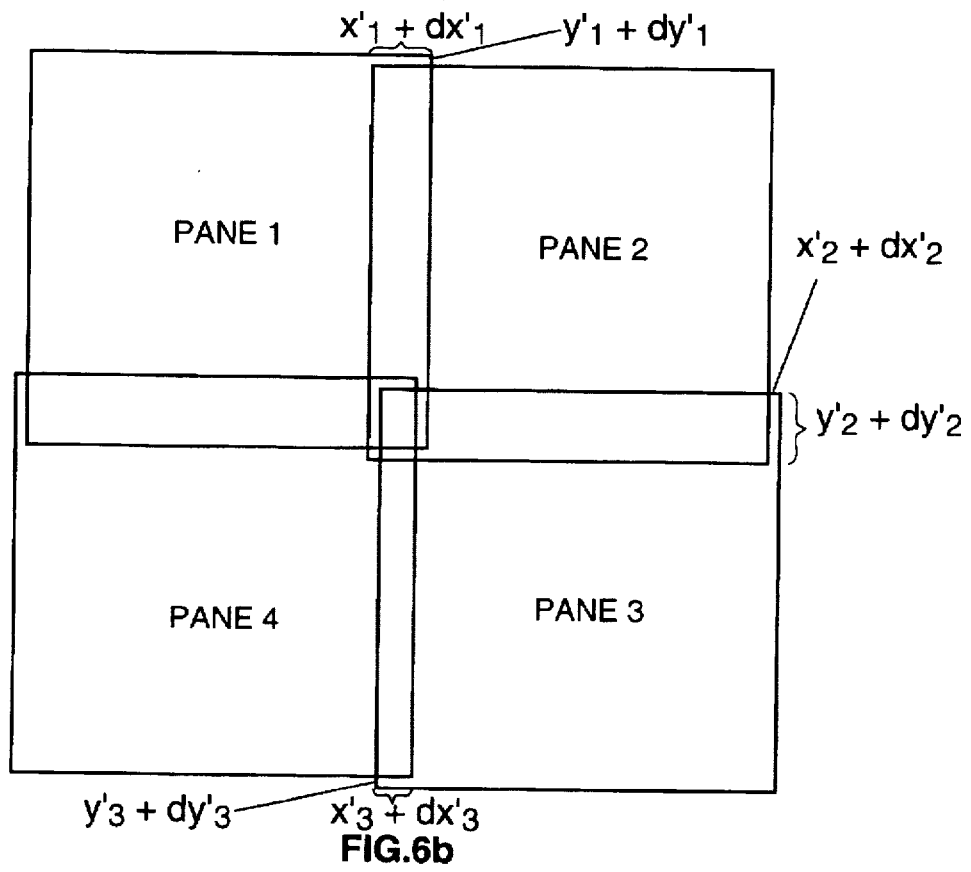

We have now produced four image panes which are corrected for distortions and are rotated such that their image axes are parallel to each other as shown in FIG. 6a. Accurate registration of these images requires a determination of the relative offsets in the x and y directions of each image pane relative to the other image panes. We then position each image pane in the computer 18 such that the four image panes correctly align with one another to form a full seamless image as shown in FIG. 6b. The preferred embodiment calculates the offsets by cross-correlating fiducial marks 81 which are located at the edges of each image pane as shown in FIG. 6a. Fiducial marks with sharp edges in both directions, such as the words LORAD CORPORATION FULL BREAST DIGITAL IMAGE, for example, are preferred for the correlation procedure.

We begin by determining the relative integer offsets between image pane 1 and image pane 2. Image pane 1 and image pane 2 are mathematically defined as $I_1(x_i, y_j)$ and $I_2 x_i, y_j)$, respectively, where $x_i = \Delta x * i$ and $x_j = \Delta y * j$ (i,j=1,N) where $\Delta x$ and $\Delta y$ are the dimension of each pixel ($\Delta x = \Delta y =$ 40 microns at the breast case for the preferred embodiment). We calculate the correlation function $C(x_m, y_n)$ between image pane 1 and image pane 2 as $$C(x_m, y_n) = \left[ \sum_{i,j=1,N} I_1^2(x_i, y_i) I_2^2(x_i + x_m, y_j + y_n) \right]^{-1/2} \sum_{i,j=1,N} I_1(x_i, y_j) I_2(x_i + x_m, y_j + y_n) \quad (4)$$

$C(x_m, y_n)$ (m,n=1,N) is a two-dimensional grid of numerical values. $C(x_m, y_n)$ has a sharp maximum value $C(X_1', Y_1')$ at the pixel location $(x_1', y_1')$. This location is also denoted as integer values $(i_1', j_1')$ where the two image pane align themselves.

The value $C(x_1', y_1')$ provides the nearest integer offset $(x_1', y_1')$ between image pane 1 and image pane 2. Higher registration accuracy can be obtained by calculating a residual fractional offset $(dx_1', dy_1')$ which further maximizes $C(x_1' + dx_1', y_1' + dy_1')$. We use an interpolation procedure which fits $C(x_1' + dx_1', y_1' + dy_1')$ to a quadratic function and then calculates the coordinate $x_1' + dx_1'$ at which $C(x_1' + dx_1', y_1')$ is maximized while holding the y-axis constant at $y_1'$. We then calculate the coordinate $y_1' + dy_1'$ at which $C(x_1', y_1' + dy_1')$ is maximized while holding the x-axis constant at $x_1'$. Following this procedure, the fractional offset $(dx_1', dy_1')$ is calculated as $$dx_1' = \frac{1}{2} \frac{C(x_1'+1, y_1') - C(x_1'-1, y_1')}{2C(x_1', y_1') - C(x_1'+1, y_1') - C(x_1'-1, y_1')} \quad (5)$$

$$dy_1' = \frac{1}{2} \frac{C(x_1', y_1'+1) - C(x_1', y_1'-1)}{2C(x_1', y_1') - C(x_1', y_1'+1) - C(x_1', y_1'-1)}$$

where $(x_1', y_1')$ is the integer offset.

We calculate the integer offset $(x_2' + dx_2', y_2' + dy_2')$ and $(x_3' + dx_3', y_3' + dy_3')$ between image pane 2 and image pane 3, and image pane 3 and image pane 4, respectively in the same manner by correlating the fiducial marks 81 located in the overlap region between these respective panes. The offsets $(x_i' + dx_i', y_i' + dy_i')$ (i=1,3) are stored in the computer 18.

5) Registration of Images

We now register the four image panes on a full breast grid $I_F(x_r, y_s)$ (r,s=1,2N) which has 2N×2N regularly spaced grid points. We begin by mapping image pane 1 given by $I_1(x_i, y_j)$ (i=1,N) directly to the upper left corner of the full grid such that $I_F(x_i, y_j) = I_1(x_i, y_j)$ (i,j=1,N) as shown in FIG. 6a. We then map image pane 2 given by $I_2(x_i, y_j)$ (i,j=1,N) onto the full grid. This is done in two steps: 1) remapping of the fractional offsets $(dx_1', dy_1')$, and 2) mapping of the integer offsets $(x_1', y_1')$. We first correct for the fractional offsets $(dx_1', dy_1')$ by remapping $I_2(x_i - dx_1', y_j - dy_1')$ (i,j=1,N) which generally falls between the pixel locations onto a regularly spaced grid $I_2(x_i, y_j)$ (i,j=1,N). This is done by calculating the value of $I_2(x_i, y_j)$ at the integer pixel location $(x_i, y_j)$ nearest to the non-integer pixel location $(x_1 - dx_1', y_j - dy_1')$. The preferred embodiment calulates this with a bilinear interpolation procedure as discussed in detail in Section 3.5.1 (pg. 58–61) of "Digital Image Warping", by George Wolberg, IEEE Computer Society Press, Los Alamitos, 1990. Higher accuracy can be achieved by using a higher-order Lagrange polynomial interpolation as discussed in Section 3.6 of the same text. We then map image pane 2, $I_2(x_i, y_j)$ (i,j=1,N), onto the full grid such that $I_F(x_i, y_j) = I_2(x_i - N*\Delta x + x_1' 1, y_j + y_1' + 1)$ (i=N-$i_1'$,2N; j=-$j_1'$,N).

We repeat the registration procedure in a similar manner for image pane 3 and image pane 4. First we correct for the fractional offsets $(dx_2', dy_2')$ and $(dx_3', dy_3')$ by remapping $I_3(x_i - dx_2', y_j - dy_2')$ (i,j=1,N) and $I_4(x_i - dx_3', y_j - dy_3')$ (i,j=1,N), each which generally fails between the pixel locations, onto a regularly spaced grid $I_3(x_i, y_j)$ (i,j=1,N) and $I_4(x_i, y_j)$ (i,j=1,N), respectively. We then map image pane 3, $I_3(x_i, y_j)$ (i,j=1,N), onto the full grid such that $I_F(x_i, y_j) = I_3(x_i - N*\Delta x + x_1' + 1, y_j - N*\Delta y + y_1' + 1)$ (i=N-$i_1'$,2N; j=N-$j_1'$,2N). We then map image pane 4, $I_4(x_i, y_j)$ (i,j=1,N), onto the full grid such that $I_F(x_i, y_j) = I_4(x_i + x_1' + 1, y_j - N*\Delta y + y_1' + 1)$ (i=-$i_1'$,N; j=N-$j_1'$,2N). The final image is then fully registered as displayed in FIG. 6b.

6) Blending

The luminance values of the pixels in the final image are finally adjusted to provide a seamless image. As discussed in preprocessing secton, the luminance values of each image pane have been normalized to each other. A sum of the two luminance values at the pixel location where two image panes overlap produces a final image where the luminance values in the overlap regions are a factor of two higher than the luminance values in the non-overlap regions. A simple blending procedure involves dividing the luminance values in the overlap regions by a factor of two to produce a seamless image.

We blend together the overlapping regions by a slightly more elaborate algorithm. We linearly weight the sum of the luminance values of the pixels in the overlap regions between image pane 1 and image pane 2 to provide a 100% weight to pixels of image pane 1 at the side of the overlap region closest to image pane 1 and a 100% weight to pixels of image pane 2 at the side of the overlap region closest to image pane 2. This is mathematically expressed as $I_F(x_i, y_j) = [(N-i)/i_1']*I_1(x_i, y_j) + [(i_1' - N+i)/i_1']*I_2(x_{i-N+1}', y_j + y_1')$ (i=N-$i_1'$,2N; j=-$j_1'$,N). This procedure seems to produce a higher quality image with a less noticable overlap region.

We repeat this procedure in a similar manner for the overlap region between image pane 2 and image pane 3 and the overlap region between image pane 3 and image pane 4.

7) Image Enhancement

The seamless digital image $I_f(x_r, Y_s)$ (r,s=1, 2N) of the full breast is processed in the computer 18 in order to optimize the contrast between features in the breast. The preferred image enhancement procedure involves a preferential enhancement of the high spatial frequency components of the image while maintaining a good balance between the low and high spatial frequency components. The enhancement procedure starts with a logarithm transform $I_{log}(x_r, Y_s) = \ln[I_f(x_r, Y_s)]$ (r,s=1, 2N) of the image in order to reduce the contrast differences of the image and to linearize the computer calculations. The high spatial frequency components of the image $I_{log}(x_r, Y_s)$ are enhanced by a procedure commonly known as "unsharp masking" where we subtract a fraction of a blurred image from the original image, $I_{enh} = I_{log} - a \cdot I_{blurred}$, where typically a=0.25. $I_{blurred}$ obtained by succesively convolving the image $I_{log}(x_r, Y_s)$ with three top hat pixel distributions of various sizes (preferred top hat pixel dimensions are 100×100, 75×75, and 125×125). This procedure is described in Section 7.4 of "Fundamentals of Digital Image Processing", by Anil K. Jain, Prentice Hall, N.J., 1989.

The contrast of the image $I_{enh}(x_r, Y_s)$ is adjusted to produce the final image. The preferred procedure uses a sigmoid function, $I_{final}(x_r, Y_s) = [1 - \exp(-\sigma(I_{enh}(x_r, Y_s) - M))]^{-1}$ where M is the mean value of the image $I_{enh}(x_r, Y_s)$ and $\sigma$ is a gain parameter. The parameters M and $\sigma$ are presently chosen by visual inspection of each image.

Figure 15:
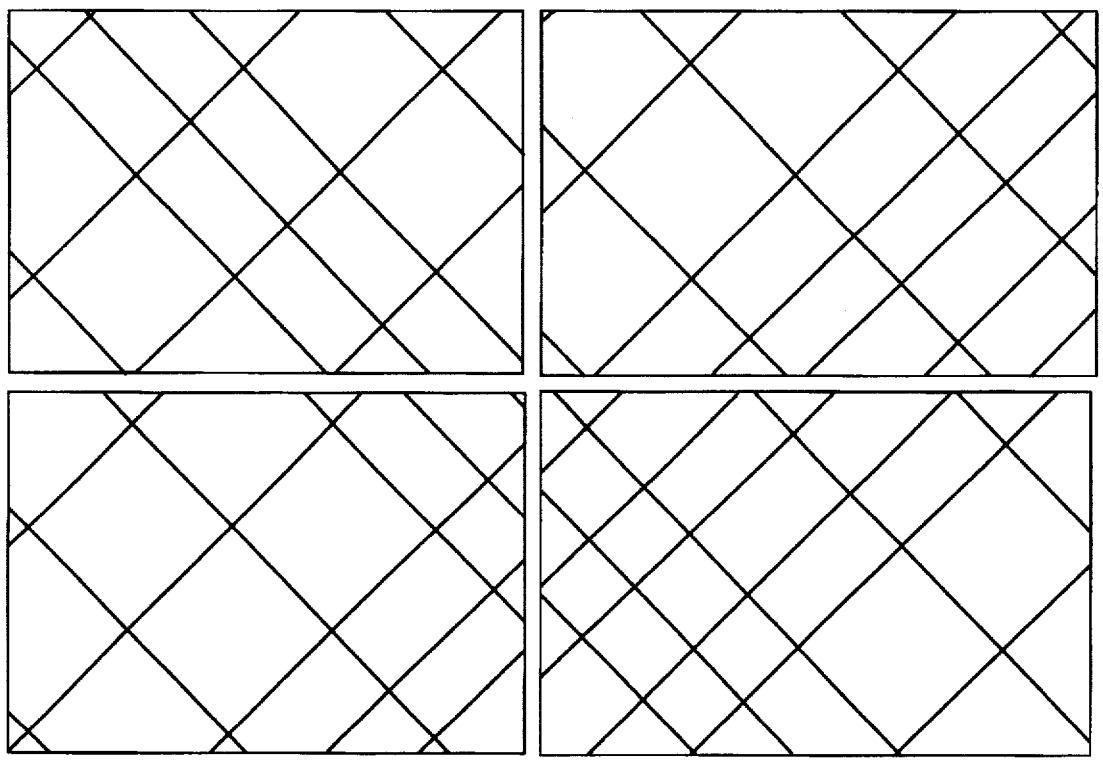
FIG. 15 shows the four image panes of a digital x-ray image acquired with the invention.
Figure 16:
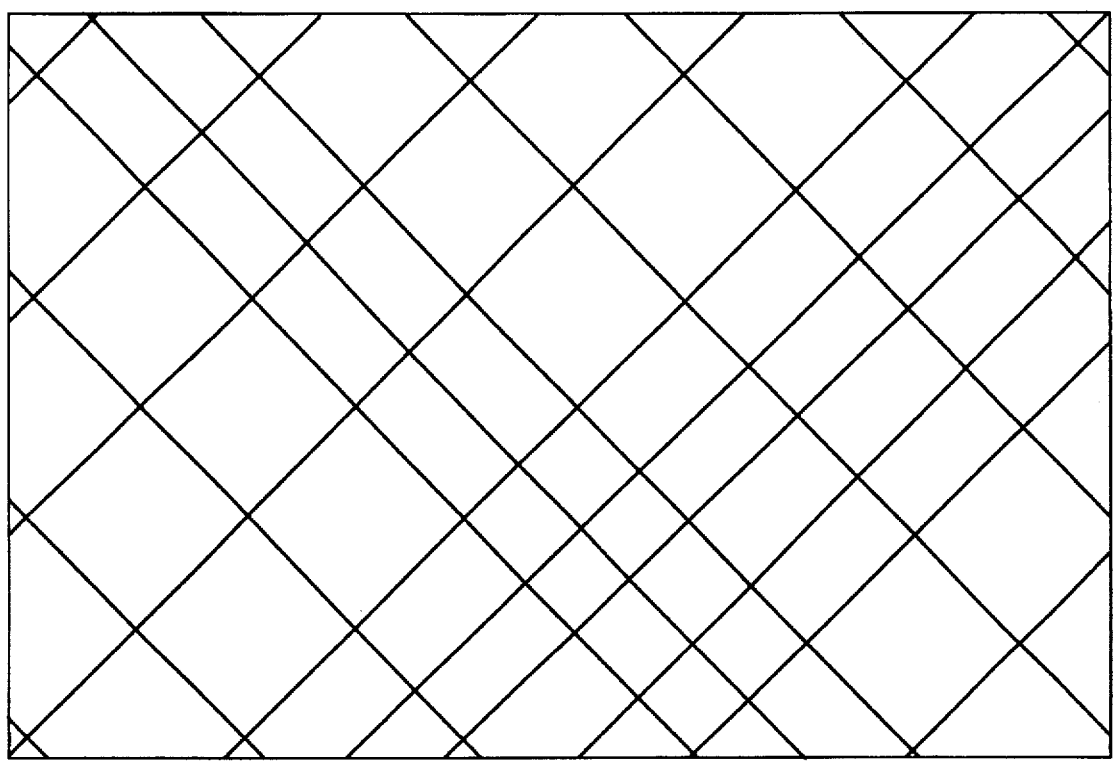
FIG. 16 shows the four image panes stitched together to produce a full seamless image.
Figure 17:
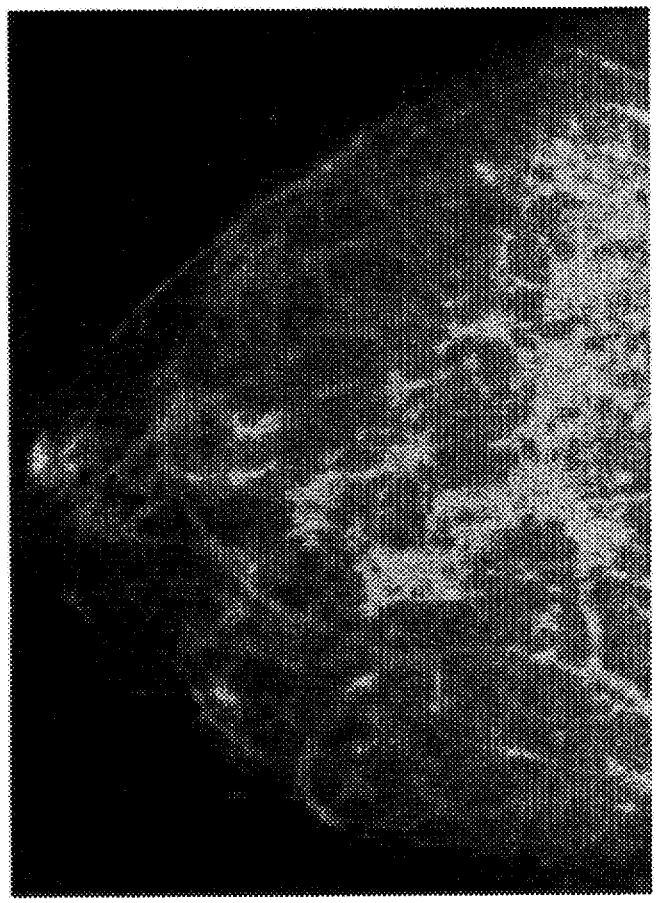
FIG. 17 shows a stitched digital x-ray image of a female breast acquired with the first preferred embodiment of the invention.

FIG. 15 shows the four image panes of a digital x-ray image acquired with the first preferred embodiment of the invention. FIG. 16 shows the four image panes stitched together to produce a full seamless image. FIG. 17 shows a stitched digital x-ray image of a female breast acquired with the first preferred embodiment of the invention. The fiducial marks 81 are evident at the periphery of the final image in FIG. 17.

Second Preferred Embodiment

Figure 7:
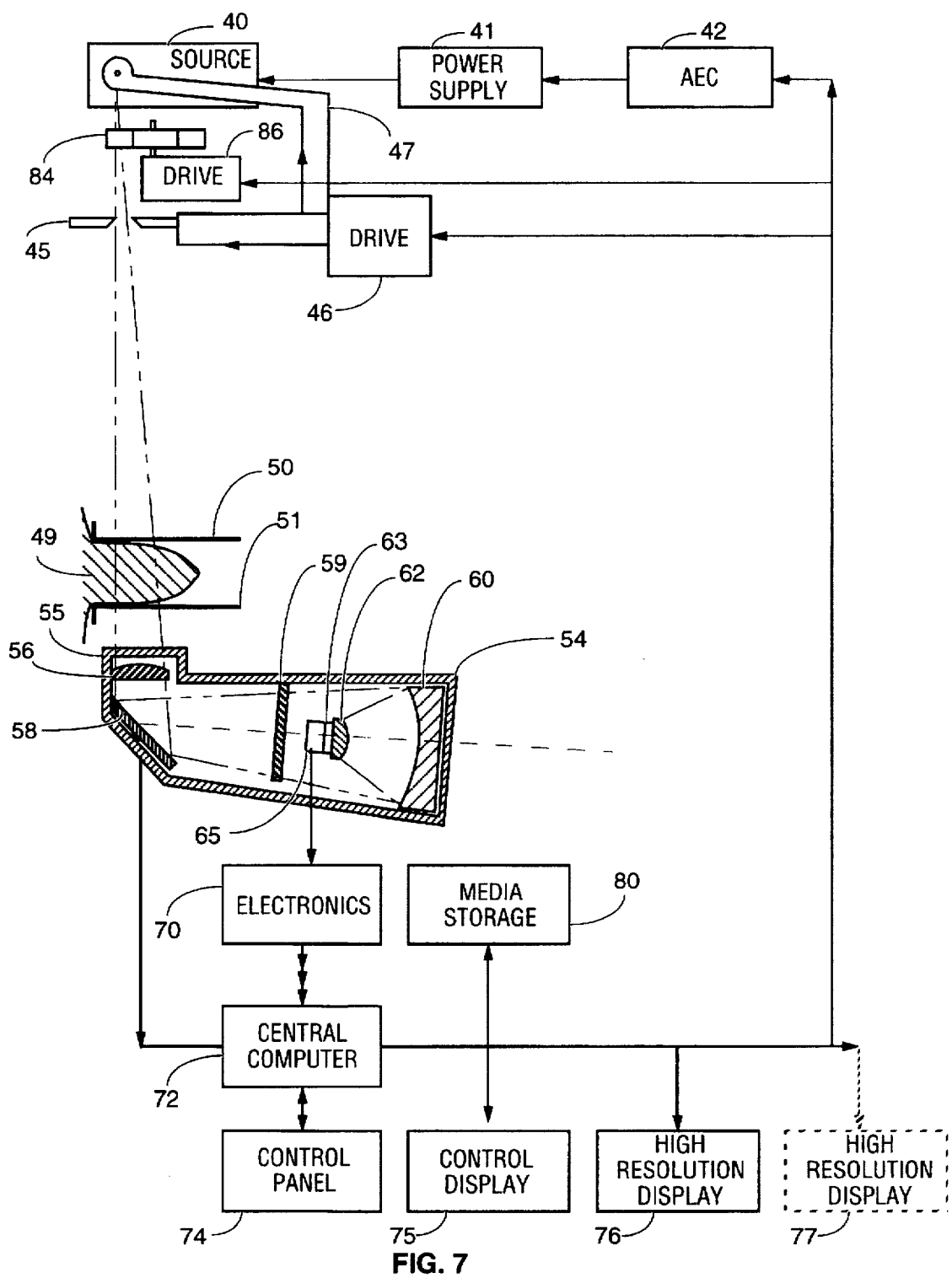
FIG. 7 is a schematic drawing showing the principal elements of a second preferred embodiment of the invention fabricated by inventors and their co-workers.

A schematic of the key elements of a second preferred embodiment of a digital mammography device is currently being fabricated by the inventors and their fellow workers is shown in FIG. 7. The device consists of an x-ray source 40, a conventional breast compression mechanism 50, and a digital detector system 54.

The preferred embodiment utilizes an x-ray source 40 which incorporates a standard Model B110/M149 Varian/ Eimac x-ray generation tube with a tungsten anode. High voltage power is applied to the x-ray source 40 with power supply 41. An x-ray filter wheel 84 has different x-ray filters, fabricated from aluminum, silver, iodine, and rhodium, for example. A specific filter in the filter wheel 84 is automatically selected by filter wheel drive 86 which is linked to the central computer 72. This embodiment locates the x-ray tube 3 at 0 elevation, aperture 45 at 15 cm, the breast tray 49 at 60 cm, and the front surface of the scintillator 55 at 63 cm.

Figure 8:
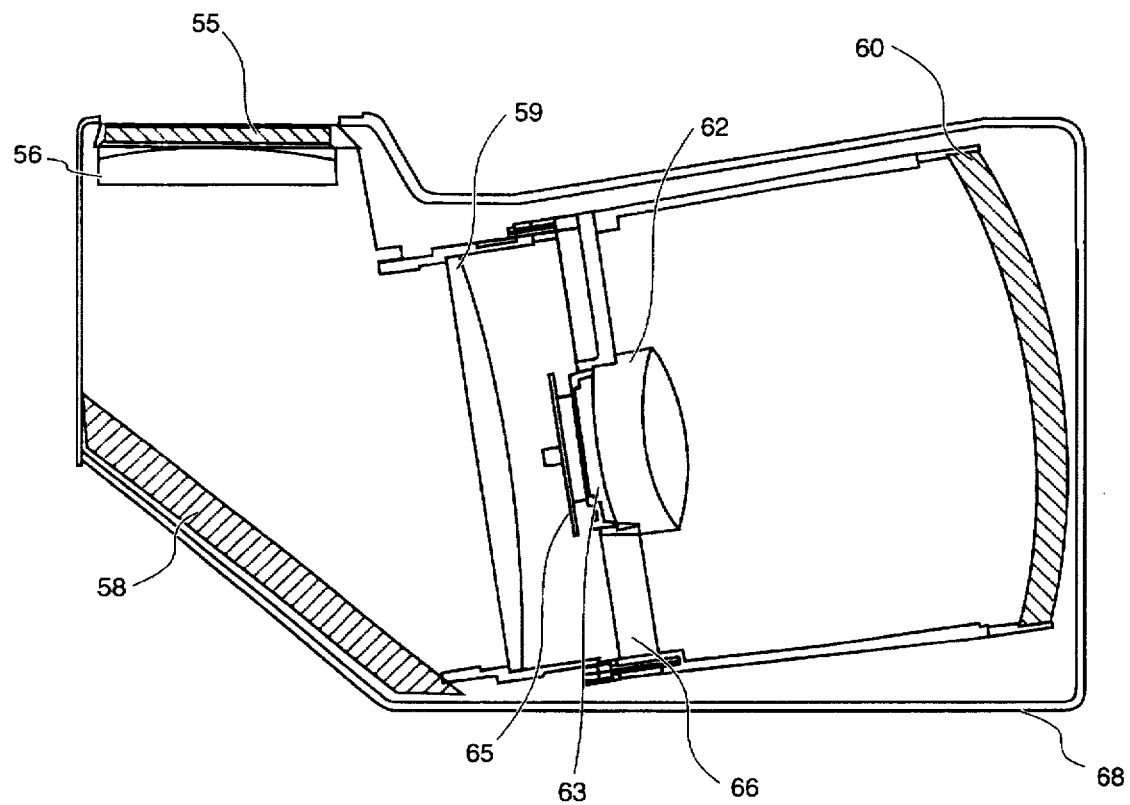
FIG. 8 is a drawing showing the principal parts of the x-ray detector assembly in the second preferred embodiment of the invention.

The digital detector assembly 54 displayed in FIG. 8 is an improved version of the digital detector assembly 15 disclosed in the first preferred embodiment. The digital detector assembly consists of a scintillator assembly 55, and a Schmidt optical system consisting a field lens 56, flat mirror 58, aspherical Schmidt corrector plate 59, spherical f/0.83 primary mirror 60 which focuses the light into a doublet lens 62, finally forming an image on a CCD array 63. The entire digital detector assembly 54 is enclosed in a sealed housing 68 to eliminate dust and ambient visible light.

Figure 9A:
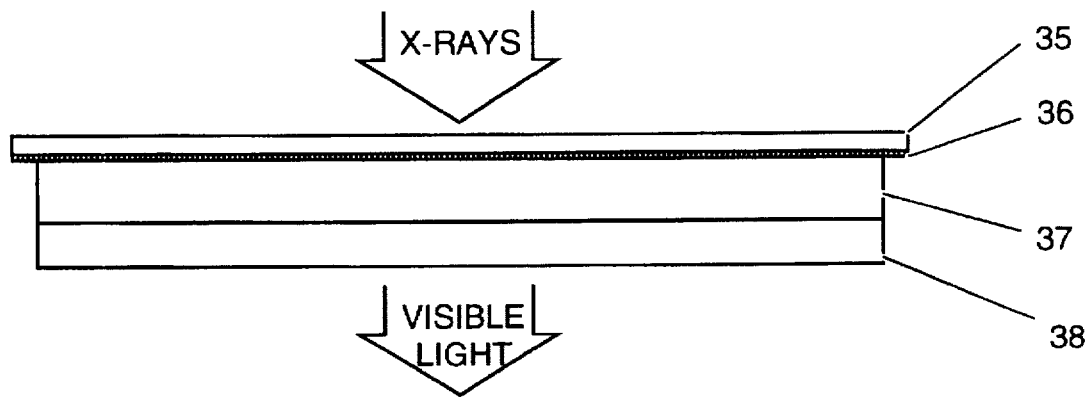
FIG. 9a–9c show three methods of fabricating an efficient x-ray to visible light converter.
Figure 9B:
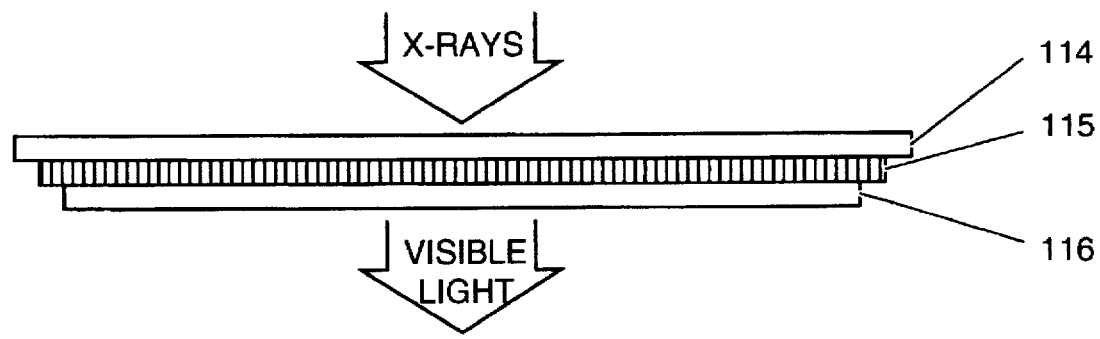
Figure 9C:
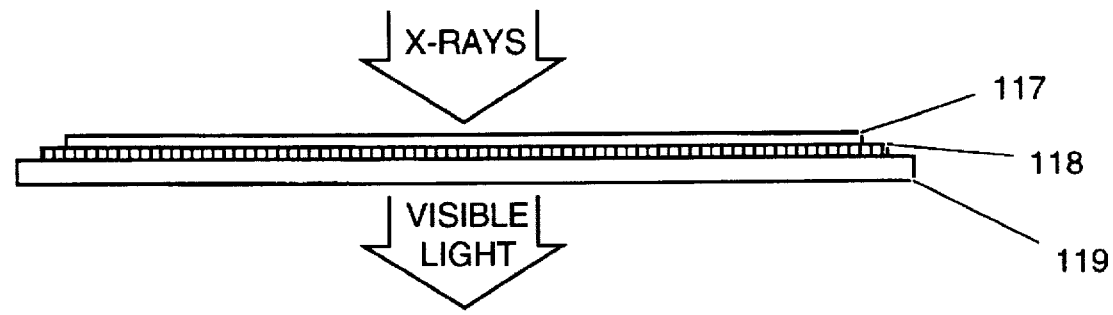

FIG. 9a–c discloses three methods for fabricating the scintillator assembly 55. Each x-ray photon striking the scintillator assembly 55 is converted into a large number of visible photons. The preferred embodiment allows the maximum number of x-rays to be absorbed by the scintillator, the maximum number of visible photons to be converted for each x-ray photon, and the maximum number of visible photons to exit the rear surface of the scintillator.

FIG. 9a displays our currently preferred method of fabricating the scintillator assembly 55. We use a 7 cm×7 cm×0.25 cm thick optically transparent scintillatot crystal 37. The preferred scintillator material 37 is a thallium-doped cesium iodide (CsI/Tl) crystal which is polished on both sides of the thickness dimension. Another possible scintillatot crystal is thallium doped sodium iodide. The fragile CsI scintillatot 37 is bonded to a 0.25 cm thick sheet of optically transparent polycarbonate 38 to provide structural rigidity. A separate 0.1 cm thick sheet of polycarbonate 35 is coated with a thin aluminum coating 36 in order to provide maximum reflectance for visible light. The aluminum coated side of the polycarbonate sheet 35 is bonded to the top of the scintillatot 37. The polycarbonate sheet 35 is then machined to a thickness of 0.025 cm in order to minimize the attenuation of x-rays passing through the sheet 35. We calculate that for 17 to 30 keV x-ray photons such as used for x-ray mammography imaging, for example, that greater than 98% of the x-rays striking the scintillator assembly 55 pass through the polycarbonate sheet 35 and the aluminum coating 36 and are absorbed in the first 200 microns of the scintillator 37 which converts each x-ray photon into a large number of visible photons. These visible photons are emitted into $4\pi$ steradians and the photons hitting the aluminum coating are reflected back towards the Schmidt optical system thus effectively doubling the visible light collected by the CCD array 63. A visible light image representing the attenuation of x-rays through the breast 49 is therefore produced at the front surface of the scintillator 37.

The second preferred embodiment utilizes a commercially available Model KAF-1000 CCD array 63 (Kodak Corporation) containing an array of 1024×1024 pixels. The size of each pixel is 24 microns×24 microns resulting in 2.5 cm×2.5 cm imaging area. The Schmidt optical system provides a magnification ratio of 2.75 between the CCD array 63 and the front surface of the scintillator 37. The separation distance of 3 cm between the breast 49 and the x-ray absorbing surface of the scintillator 37 produces a slight geometrical magnification of 1.05 of an object at the breast tray 51. In addition, this separation distance contributes to the reduction of the background signal produced by x-rays scattered by the breast 49. This results in an equivalent pixel size of 66 microns×66 microns at the scintillator assembly 55 and an equivalent pixel size of 63 microns×63 microns at the breast tray 51. The imaging area is then 6.7 cm×6.7 cm at the scintillator assembly 55 and 6.5 cm×6.5 cm at the breast tray 51. The spectral response characteristics of the CCD array 63 are selected to provide the most efficient detection of the visible photons emitted by the scintillator assembly 55.

A driver/preamplifier electronics assembly 65 is provided at the CCD 63, with cables leading to external detector electronics assembly 70 which contains analog-to-digital conversion circuitry to convert the analog CCD data into 12-bit digital values at a 5 MHz readout rate. This digital data is then stored in the central computer 72. The central computer 72, a commercially available 586AT, is equipped with a high resolution display monitor 76, a very high resolution display monitor 77 to view the final images, and a media storage device 80 to store the images. A separate control panel 74 used to control the x-ray source 40 is linked with the central computer 72.

Figure 10:
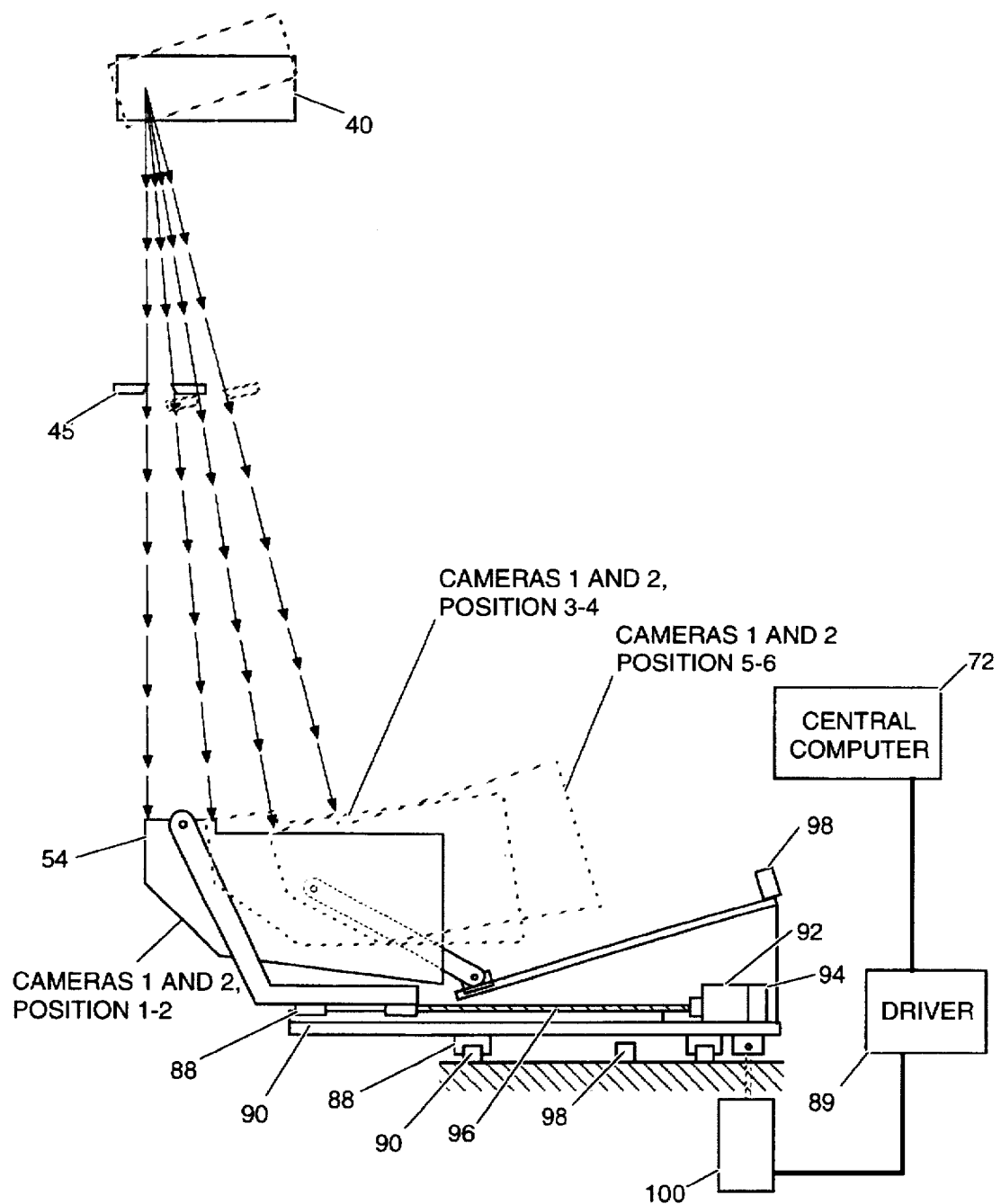
FIG. 10 is a side view of the invention which shows the different positions of the digital detector assembly.
Figure 11:
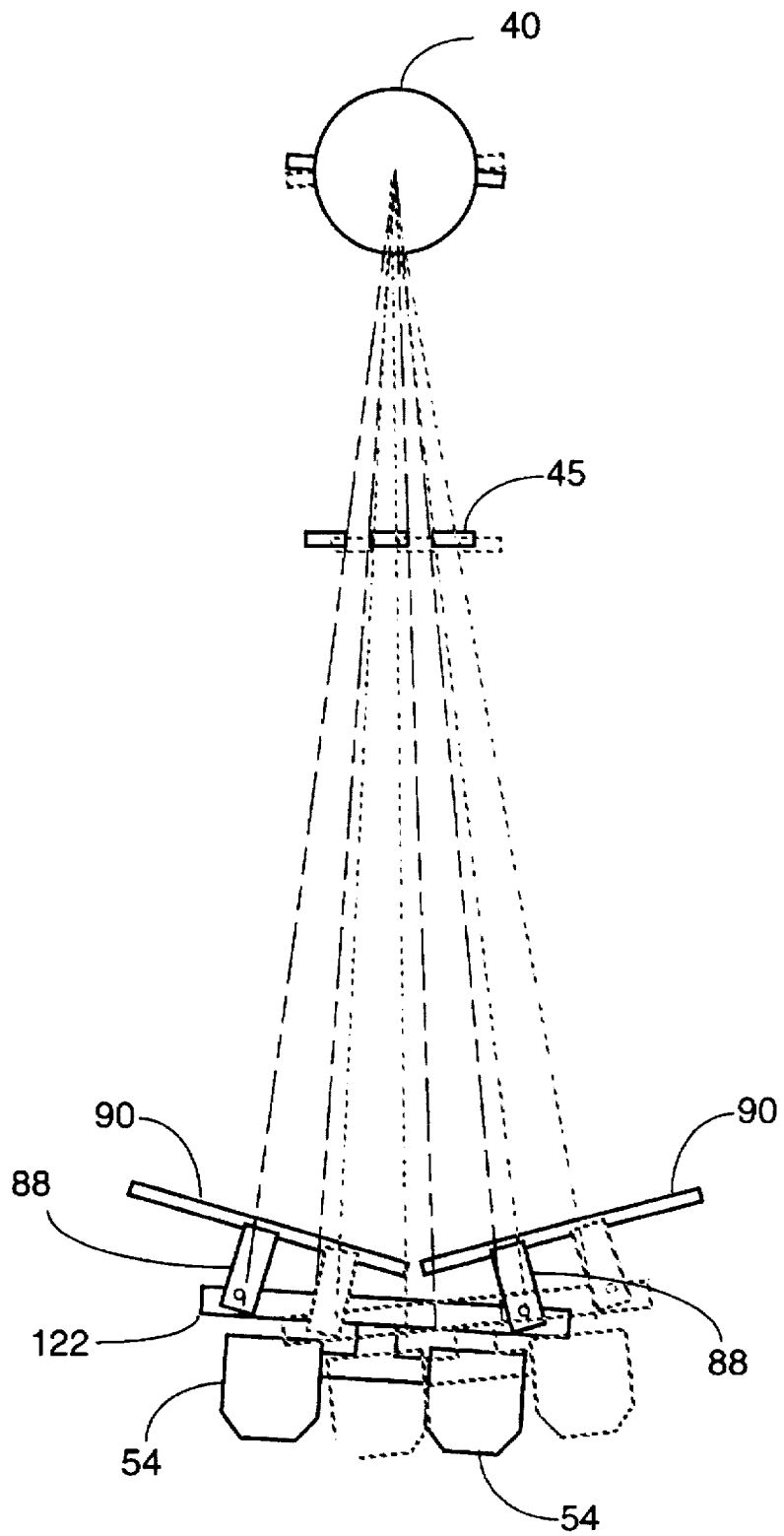
FIG. 11 is an end view of the invention which shows the different positions of the digital detector assembly.

The second preferred embodiment uses two identical digital detector assemblies 54 which simultaneously image different areas of the breast in order to reduce the imaging time. FIGS. 10 and 11 show the side and end view of the detector assemblies 54. The x-ray source 40, aperture 45, and the two digital detector assemblies 54 move relative to the clamped breast 49 to sequentially image sixteen individual sections (eight sections per camera) of the breast 49. FIGS. 10 and 11 show the different positions of the two detector assemblies 54. The front surfaces of the scintillator assemblies 55 in the two digital detector assemblies 54 move along a plane while the front surfaces of the scintillator assemblies 55 tilt so as to always remain normal to the x-ray paths. This feature results in improved image quality.

FIGS. 10 and 11 show the different positions of detectors 54. The two detectors 54 are rigidly mounted to a frame 122 which moves with LM Corporation Type HK ball slides 88 mounted on HK Corporation rails 90 which are mounted to the mammography unit frame. A separate drive 46 is used to sequentially position the x-ray source 40 as the position of the detector assemblies 54 changes. The drive 46 also positions aperture 45 with respect to the detectors 54 and the x-ray source 40. Aperture 45 contains two apertures to confine the x-ray beam within the areas defined by the two scintillator assemblies 55. Rapid camera motion is produced in both directions by servo motors 100 driving high lead angle ball screws 96. The servo motors are controlled by the central computer 72 through driver 89. Preferred embodiment operations employ Reliance Electro-Craft E-3622-H-FOOAN and E-3629-H-FOOAN brushless servomotors with 1000 line encoders, Electro-Craft BDC-12 and BDC-25 brushless drives 92. Accurate position sensing, provided by encoders 94, is provided to control the detector postions. Limit switches 98 are used for travel limits and over travel protection.

Figure 12A:
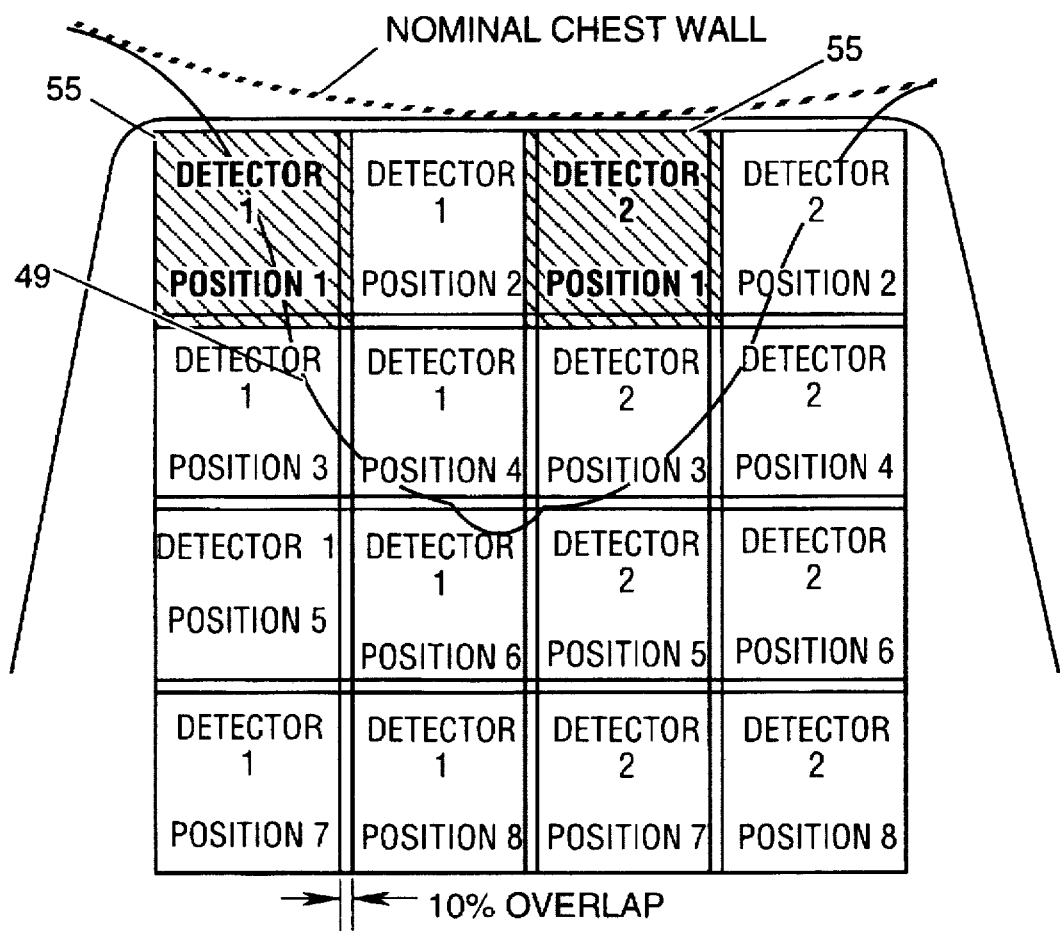
FIG. 12a shows the different image pane positions of the second preferred embodiment of the invention.
Figure 12B:
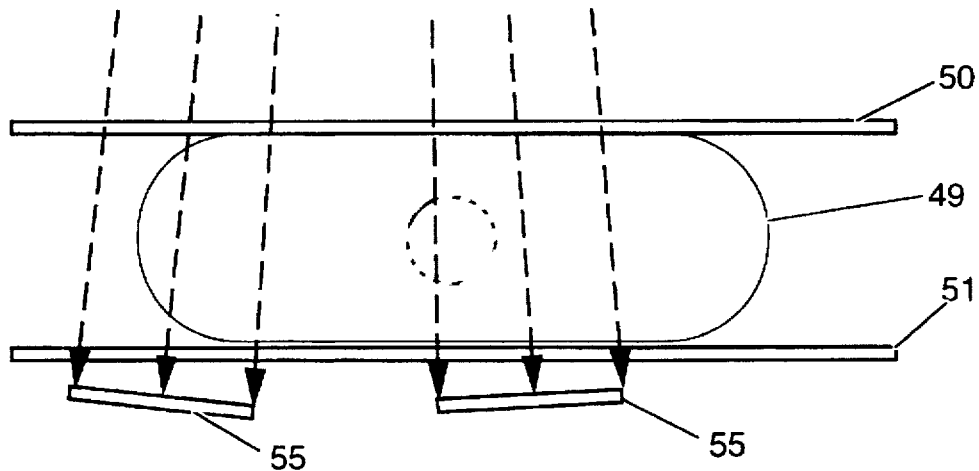
FIG. 12b shows x-ray paths for the two camera positions.

FIG. 12a demonstrates shows the sixteen image pane positions with respect to the breast tray 24. The two detectors simultaneously image the breast in the first position and then sequentially move to each of the next seven positions, imaging the breast at each position. The imaging areas of the sixteen image panes, corresponding to the area of the scintillator assembly 55, overlap by 10% to facilitate the stitching algorithm in order to provide a single seamless image of the full breast. FIG. 12b shows the different x-ray paths provided by the dual aperture 45 which strike the two scintillator assemblies 55.

Data acquisition is same as described previously. The sixteen image panes are then stitched as described previously. The detector positions in the second preferred embodiment are accurately repeatable so that the offset and distortion constants are determined only once and not for each breast image.

Figure 13B:
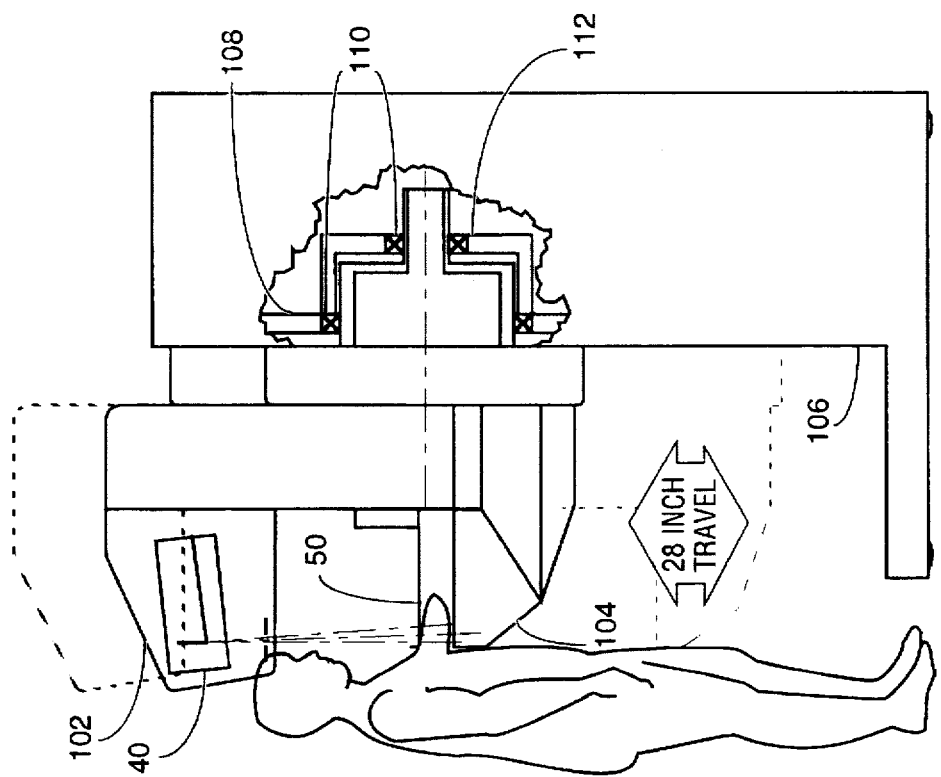
FIG. 13a and 13b show the front and side view of the invention.
Figure 13A:
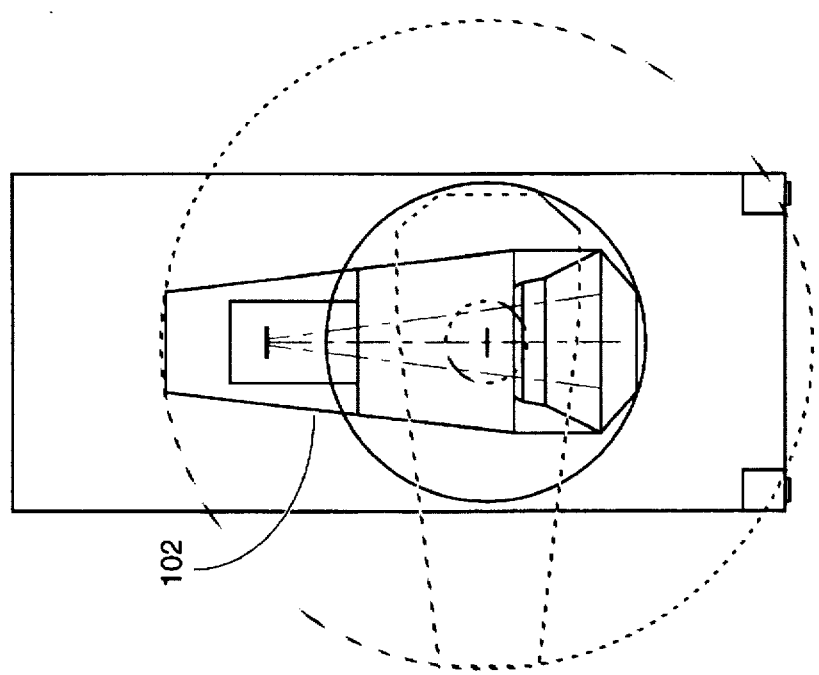

FIG. 13a and 13b show the front and side view of the packaged invention. The entire x-ray source 40, compression device 50, and detector assemblies 54 are mounted to a C arm 102. The C arm pivots to allow mediolateral and cranial-caudal x-ray views commonly acquired in fmammography examinations. In the preferred embodiment, the C arm 102 is attached to the base assembly 106 via a pair of rotary bearings 110 which are mounted on a shaft 112 attached to a slide mounted vertical travel carriage 108. The vertical travel carriage 108 allows the height adjustment of the C arm 102 for patient interface.

Alternate Embodiments

Figure 14A:
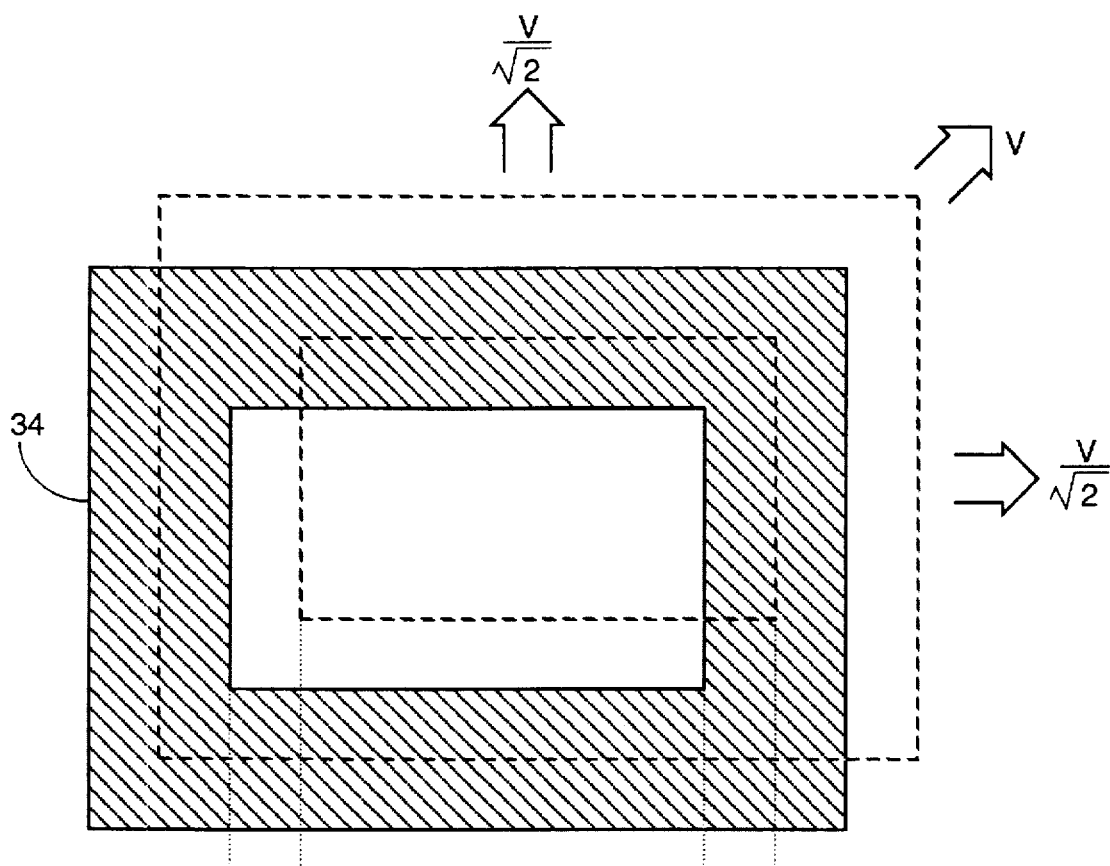
FIG. 14a and 14b illustrate the principle of the moving x-ray apodizer.
Figure 14B:
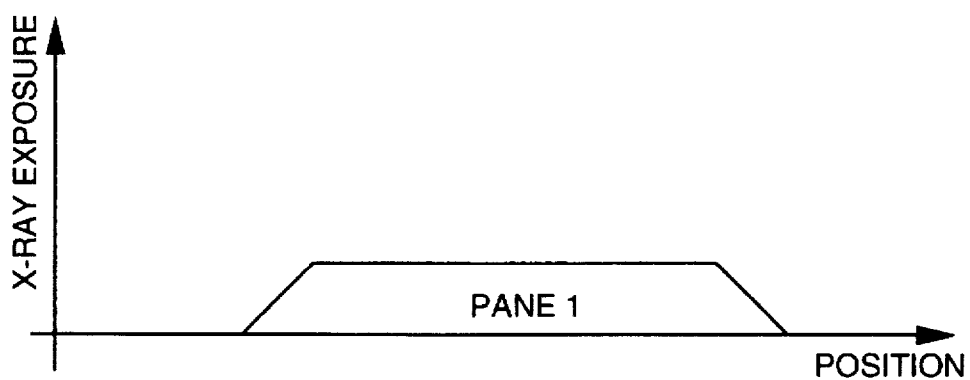

The attenuator 30 described in FIG. 4 has functioned well in the invention. However, the moderately broad x-ray spectrum from the x-ray source passing through the attenuator 30 results in a phenomenom commonly known as beam hardening which is a variation of x-ray attenuation as a function of x-ray energy. This has resulted in final images which display a slight variation of the luminance in the overlap region compared to the non-overlap region (see combining of images). FIG. 14a illustrates an alternate attenuator 34 which we have fabricated and implemented which is independent of x-ray energy, thereby alleviating the problem of beam hardening. We have tested this attenuator 34 in the first preferred embodiment of the invention with excellent results. The attenuator 34 is positioned at the aperture 6 as shown in FIG. 1. Attenuator 34 is fabricated with 0.5 cm thickness of lead which substantially blocks x-rays. The inner dimension of the attenuator 34 is 7.7 cm×10 cm as displayed in FIG. 14a. The attenuator 34 is initial positioned before each image pane exposure so that the shadow cast by the attenuator 34 completely obscures the overlap region of the image pane. The outer dimensions of the attenuator 34 are large enough to completely block all x-rays in the periphery. The attenuator 34 moves at a constant speed v in the direction illustrated in FIG. 14a during the approximately 1 sec x-ray exposure. This results in an x-ray exposure which decreases linearly as one moves through the overlap region, as shown in FIG. 14b. Attenuator 34 is positioned with respect to each image pane before each image pane exposure by moving the aperture 6 with the linkage system 5. The total exposure in the overlap regions which a sum of exposures of the individual image panes is then reduced to the average exposure level of each pane. Even where the four panes overlap the exposure is reduced to the average exposure level of each image pane.

FIG. 10b discloses an alternate method for fabricating the scintillator assembly 55. This method involves coating a 7 cm×7 cm×0.25 mm thick sheet of berylium or polycarbonate 114 with a thin layer of aluminum 115 to provide maximum reflectance for visible photons. A 200 micron thick layer of dendritic cesium iodide 116 is then coated onto the aluminum coated 115 side of the berylium sheet. This allows a minimum number of x-ray photons to be absorbed by the berylium and the maximum number of x-ray photons to be converted each to a large number of visible photons. The aluminum coating helps to direct a maximum amount of these visible photons towards the rear of the scintillator assembly 55.

FIG. 10c discloses a third method for fabricating the scintillator assembly 55. This embodiment provides a 200 micron thick layer of dendritic cesium iodide 118 on a 7 cm×7 cm×0.1 cm thick sheet of optical glass 119. A thin layer of aluminum 117 is then coated onto the dendritic cesium iodide. This allows the maximum number of x-ray photons to be converted into visible light and allows these visible photons to pass through the optical glass with the minimum amount of attenuation towards the rear of the scintillator assembly 55.

The present invention requires manual selection of x-ray exposure times for a given x-ray energy and filter combination. The exposure time also depends on the breast size and composition. An alternate embodiment incorporates an x-ray source 40 and power supply 41 controlled by an automatic exposure control (AEC) circuit 42 utilizing feedback from a pre-exposure pulse. The AEC circuit is presently used on Lorad's commercially available M3 mammography unit. The approximately 1 msec pre-exposure pulse is acquired directly before the main exposure sequence by positioning the one of the detectors 54 at the center of the breast. The computer 72 uses the luminance value of the pre-pulse exposure to decide the correct x-ray exposure for a given x-ray energy and filter combination.

An alternate embodiment to the bolus material described with reference to FIG. 4b involves an adjustable x-ray mask 130, located above aperture 6 shown in FIG. 1. The mask 130 is fabricated from a material which substantially attenuates x-rays such as 0.5 cm of lead, for example. The mask 130 is adjusted after the breast 1 is positioned and compressed by the compression mechanism 2 so as to block x-rays at the periphery of the breast 1. The mask 130 is designed to be continuously deformable in order to position around the periphery of the various breast sizes and shapes.

There are several alternate embodiments for improving the quality of the stitching procedure and reducing the stitching time. The correlation analysis can be performed only on the small area surrounding the fiducial marks. The fiducial marks could be put either directly on the breast compression plate, which is subject to deformation, or on a separate dedicated frame. The distortion correction and the registration can be done at the same time to reduce the stitching time.

The preferred embodiment performs the correlation integral $C(x_1'+dx_1', y_1'+dy_1')$ in the spatial domain. This is computationally efficient when the positioning uncertainty between panes is limited to a few pixels. The correlation procedure can also be done in the spatial frequency domain by multiply two-dimensional Fourier of the areas.

The relative position of the panes can also be determined by a fiducial mask permanently placed in the x-ray path passing through the breast which superimposes a low level contrast pattern to the breast image. After stitching the image panes, the pattern due to the fiducial mask can be removed from the final image without noticeable image degradation because of the low contrast of the mask. This is done by dividing the breast image by the fiducial mask image resampled to align its grid with the breast image grid, and multiplying by the average luminance of the fiducial mask image.

There are several alternate embodiments with regard to the design features of the second preferred embodiment. The x-ray source 40 and aperture 45 may be provided by a mechanical linkage such as a chain or cable drive. The detectors 54 can be positioned using curved rails with grooved wheels and driven with AC or DC motors with linear position sensors. The detectors 54 can be moved with standard ball screw actuators, belt or cable drives, or pneumatic cylinder actuators. An alternate embodiment for the C arm 102 consists of a large rotation shaft and bearing set, with the detectors 54 inside the base unit and the optical path passing inside the bearing set.

While the above description contains many specifications, the reader should not construe these as limitations on the scope of the invention, but merely as exemplifications of preferred embodiments thereof. Those skilled in the art will envision many other possible variations are within its scope. Accordingly, the reader is requested to determine the scope of the invention by the appended claims and their legal equivalents, and not by the examples which have been given.

We claim:

1. A digital x-ray mammography device comprising:
  a) a frame,
  b) an x-ray source mounted on said frame,
  c) a breast clamp adapted to position a breast on said frame in a fixed position with respect to said source,
  d) an x-ray aperture movable mounted, with respect to said source, on said frame,
  e) an x-ray detector movable mounted, with respect to said source, on said frame and aligned with respect to said aperture so as to detect x-ray beams from said x-ray source passing through said aperture, said detector including:
     (1) an x-ray to visible light medium for converting x-rays to visible light,
     (2) a detector array, and
     (3) an optical system for directing visible light onto said detector array to produce images on said detector array,
  a positioning system adapted to sequentially position said aperture and said x-ray detector in order to provide a plurality of overlapping x-ray beam paths extending radially from said x-ray source to said conversion surface, said overlapping beam paths defining corresponding overlapping breast regions,
  g) a data acquisition system for acquiring digital image data from said detector array for each of said overlapping breast regions, said digital image data for each of said overlapping breast regions defining an image pane,
  h) a computer programmed with a stitching algorithm for stitching together said image pane create a composite x-ray image of at least a portion of said breast, the programmed computer performing the functions of:
     (1) registering each image pane onto a common pattern such that a portion of each image pane overlaps a portion of at least one other image pane,
     (2) blending overlapped portions of said image panes to create the composite x-ray image of at least a portion of said breast.

2. A mammography device as in claim 1 wherein said optical system means comprises a Schmidt camera.

3. A mammography device as in claim 2 wherein said Schmidt camera comprises a spherical mirror, a Schmidt corrector plate, a CCD array, and an analog-to-digital conversion means for converting analog data from said CCD chip to digital data.

4. A mammography device as in claim 3 wherein said Schmidt camera also comprises a doublet lens located adjacent to said CCD array.

5. A mammography device as in claim 3 wherein said Schmidt camera also comprises a lens located adjacent to said conversion surface.

6. A mammography device as in claim 1 wherein said conversion surface comprises a phosphor screen.

7. A mammography device as in claim 6 and further comprising a pellicle mirror through which all of said x-ray paths pass and said camera is focused on said conversion surface through a reflection of said visible light off said pellicle mirror.

8. A mammography device as in claim 1 wherein said conversion surface is a scintillator assembly.

9. A mammography device as in claim 8 wherein said scintillator assembly comprises a scintillator crystal sandwiched between a first substrate transparent to visible light and a second substrate transparent to x-rays and reflective to visible light.

10. A mammography device as in claim 9 wherein said scintillator crystal is a doped cesium iodide crystal.

11. A mammography device as in claim 9 wherein said scintillator crystal is a doped sodium iodide crystal.

12. A mammography device as in claim 8 wherein said scintillator assembly comprises a substrate transparent to x-rays and coated with dendritic cesium iodide.

13. A mammography device as in claim 8 wherein said scintillator assembly comprises a substrate transparent to visible light and coated with dendritic cesium iodide.

14. A mammography device as in claim 1 wherein said positioning means is arranged to pivot said frame and said detector in arcs about said source so that each of said plurality of x-ray beam paths are approximately equal in length.

15. A mammography device as in claim 1 wherein said x-ray aperture comprises an apodizer means for reducing x-ray flux in said overlapping regions of said beam paths.

16. A mammography device as in claim 15 wherein said apodizer means comprises a plurality of strips comprised of a moderate attenuator of x-rays.

17. A mammography device as in claim 15 wherein said apodizer means comprises an apodizer frame comprised of a substantially total attenuator of x-rays and a means for moving said apodizer frame during x-ray exposure so as to produce x-ray beam paths with reduced x-ray flux in said overlapping regions of said beam paths.

18. A mammography device as in claim 1 wherein said computer means is programmed to calculate a set of calibration values from image data obtained with said breast replaced with a calibration grid.

19. A mammography device as in claim 18 wherein said computer means is programmed with a stitching algorithm which:
   a) organizes and preprocesses said digital image data to define a plurality of overlapping image panes defining overlapping sections,
   b) corrects for distortion in each of said plurality of image panes utilizing at least a portion of said calibration values,
   c) calculates at least one correlation function for overlapping sections of said image panes,
   d) generates alignment coordinates with respect to each overlapping section,
   e) utilizes alignment coordinates to align all of said plurality of image panes, and
   f) adjusts luminance values in said overlapping sections to provide a seamless image.

20. The digital x-ray mammography device of claim 1, including further programming for the programmed computer for performing the function of aligning each image pane with each other image pane before registering each such image pane.

21. The digital x-ray mammography device of claim 1, including further programming for the programmed computer for performing the function of determining a relative registration offset of each image pane with respect to each other image pane before registering each such image pane.

22. The digital x-ray mammography device of claim 1, wherein each image pane comprises a plurality of pixels each having a luminance value, and the function of blending includes combining corresponding overlapping pixels from said overlapping portions of said image pane and adjusting the luminance of said combined corresponding overlapping pixels to produce an essentially seamless composite x-ray image of at least a portion of said breast.

23. The digital x-ray mammography device as in claim 1, wherein said common pattern comprises a grid.

24. A computer program residing on a computer-readable medium, for stitching together a plurality of x-ray image panes to create a composite x-ray image of at least a portion of a body organ, the computer program comprising instructions for causing a computer to:
   a. register each image pane onto a common pattern such that a portion of each image pane overlaps a portion of at least one other image pane,
   b. blend overlapped portions of said image panes to create the composite x-ray image of at least a portion of said body organ, wherein each image pane comprises a plurality of pixels each having a luminance value,
   c. combine corresponding overlapping pixels from said overlapping portions of said image panes, and
   d. adjust the luminance of said combined corresponding overlapping pixels to produce an essentially seamless composite x-ray image of at least a portion of said body organ.

25. The computer program according to claim 24 the computer program comprising instructions for causing a computer to align each image pane with each other image pane before registering each such image pane.

26. The computer program according to claim 24, the computer program comprising instructions for causing a computer to determine a relative registration offset of each image pane with respect to each other image pane before registering each such image pane.

27. A digital x-ray mammography device comprising:
   a) a frame,
   b) a single x-ray source mounted on said frame,
   c) a breast clamp adapted to position a breast on said flame in a fixed position with respect to said source,
   d) at least two x-ray apertures movably mounted, with respect to said source, on said frame,
   d) at least two x-ray detector movably mounted, with respect to said source, on said frame and aligned with respect to said aperture so as to detect x-ray beams from said x-ray source passing through said aperture, each of said at least two detectors including:
      (1) a conversion element for converting x-rays to visible light,
      (2) a detector array, and
      (3) an optical system adapted to focus visible light from said conversion element onto said detector array to produce images on said detector array,
   f) a positioning system adapted to sequentially position said apertures and said x-ray detectors in order to provide a plurality of overlapping x-ray beam paths between said single x-ray source and said x-ray detectors, each of said overlapping beam paths extending radially from said single x-ray source, through one of said apertures, through a portion of said breast and into said conversion element, and each of said overlapping beam paths defining a corresponding overlapping breast region,
   g) a data acquisition system for acquiring digital image data from said detector array for each of said overlapping breast regions, said image data for each of said overlapping breast regions defining an image pane,
   h) a computer programmed with a stitching algorithm for stitching together said image panes to create a composite x-ray image of at least a portion of said breast, the programmed computer performing the functions of:
      (1) registering each image pane onto a common pattern such that a portion of each image pane overlaps a portion of at least one other image pane,
      (2) blending overlapped portions of said image panes to create the composite x-ray image of at least a portion of said breast.

28. A mammography device as in claim 27 wherein each of said optical system means comprises a Schmidt camera.

29. A mammography device as in claim 28 wherein each of said Schmidt cameras comprises a spherical mirror, a Schmidt corrector plate, a CCD array, and an analog-to-digital conversion means for converting analog data from said CCD chip to digital data.

30. A mammography device as in claim 29 wherein each of said Schmidt camera also comprises a doublet lens located adjacent to said CCD array.

31. A mammography device as in claim 29 wherein each of said Schmidt camera also comprises a lens located adjacent to said conversion element.

32. A mammography device as in claim 27 wherein each of said conversion element comprises a phosphor screen.

33. A mammography device as in claim 32 and further comprising a pellicle mirror through which all of said x-ray paths pass and each of said cameras is focused on said conversion element through a reflection of said visible light off said pellicle mirror.

34. A mammography device as in claim 27 wherein said conversion element is a scintillator assembly.

35. A mammography device as in claim 34 wherein said scintillator assembly comprises a scintillator crystal sandwiched between a first substrate transparent to visible light and a second substrate transparent to x-rays and reflective to visible light.

36. A mammography device as in claim 35 wherein said scintillator crystal is a doped cesium iodide crystal.

37. A mammography device as in claim 35 wherein said scintillator crystal is a doped sodium iodide crystal.

38. A mammography device as in claim 34 wherein said scintillator assembly comprises a substrate transparent to x-rays and coated with dendritic cesium iodide.

39. A mammography device as in claim 34 wherein said scintillator assembly comprises a substrate transparent to visible light and coated with dendritic cesium iodide.

40. A mammography device as in claim 27 wherein said positioning means is arranged to pivot said frame and said detector in arcs about said source so that each of said plurality of x-ray beam paths are approximately equal in length.

41. A mammography device as in claim 27 wherein each of said x-ray apertures comprises an apodizer means for reducing x-ray flux in said overlapping regions of said beam paths.

42. A mammography device as in claim 41 wherein said apodizer means comprises a plurality of strips comprised of a moderate attenuator of x-rays.

43. A mammography device as in claim 41 wherein said apodizer means comprises an apodizer frame comprised of a substantially total attenuator of x-rays and a means for moving said apodizer frae during x-ray exposure so as to produce x-ray beam paths with reduced x-ray flux in said overlapping regions of said beam paths.

44. A mammography device as in claim 27 wherein said computer means is programmed to calculate a set of calibration values from image data obtained with said breast replaced with a calibration grid.

45. A mammography device as in claim 44 wherein said computer means is programmed with a stitching algorithm which:
  a) organizes and preprocesses said digital image data to define a plurality of overlapping image panes defining overlapping sections,
  b) corrects for distortion in each of said plurality of image panes utilizing at least a portion of said calibration values,
  c) calculates at least one correlation function for overlapping sections of said image panes,
  d) generates alignment coordinates with respect to each overlapping section,
  e) utilizes alignment coordinates to align all of said plurality of image panes, and
  f) adjusts luminance values in said overlapping sections to provide a seamless image.

46. A computer program residing on a computer-readable medium, for stitching together a plurality of x-ray image panes to create a composite x-ray image of at least a portion of a body organ, the computer program comprising instructions for causing a computer to:
  a. align each image pane with each other image pane,
  b. determine a relative registration offset of each aligned image pane with respect to each other aligned image pane,
  c. register each image pane onto a common pattern using the relative registration offset such that a portion of each image pane overlaps a portion of at least one other image pane, and
  d. blend overlapped portions of said image panes to create the composite x-ray image of at least a portion of said body organ.

47. A digital x-ray mammography device comprising:
  a) a frame,
  b) an x-ray source mounted on said frame,
  c) a breast clamp means for positioning a breast on said frame in a fixed position with respect to said source,
  d) an x-ray aperture means movable mounted, with respect to said source, on said frame for confining x-rays radiating from said source into defined x-ray beams,
  e) an x-ray detector movably mounted, with respect to said fixedly mounted x-ray source, on said frame and movably aligned so as to detect said defined x-ray beams from said x-ray source passing through said apemare means, said detector comprising an x-ray to visible light medium and defining an x-ray to visible light conversion surface and comprising a detector array and an optical system focused approximately on said conversion surface for directing light to said detector array and producing images on said detector array,
  f) a positioning means for sequentially positioning said aperture and said x-ray detector in order to provide a plurality of overlapping x-ray beam paths between said x-ray source and said conversion surface of said x-ray detector, each of said overlapping beam paths extending radially from said x-ray source, through said aperture, through a portion of said breast and through said conversion surface, and each of said overlapping beam paths defining a corresponding overlapping breast region,
  g) a data acquisition means for acquiring digital image data from said detector array for each of said overlapping breast regions, said image data for each of said overlapping breast regions defining an image pane,
  h) a computer programmed with a stitching algorithm for stitching together said image panes to create a composite x-ray image of at least a portion of said breast, the programmed computer performing the functions of:
    (1) registering each image pane onto a common pattern such that a portion of each image pane overlaps a portion of at least one other image pane, (2) blending overlapped portions of said image panes to create the composite x ray image of at least a portion of said breast.

48. A digital x-ray mammography device comprising:
a) a frame,
b) a single x-ray source mounted on said frame,
c) a breast clamp means for positioning a breast on said frame in a fixed position with respect to said source,
d) at least two x-ray aperture means movably mounted, with respect to said source, on said frame for confining x-rays radiating from said source into defined x-ray beams,
e) at least two x-ray detectors movably mounted, with respect to said source, on said frame and aligned with respect to said aperture so as to detect x-ray beams from said x-ray source passing through said aperture, each of said at least two detectors including:
  (1) an x-ray to visible light medium having an x-ray to visible light conversion surface,
  (2) a detector array, and
  (3) an optical system focused approximately on said conversion surface for directing light onto said detector array to produce images on said detector array,
f) a positioning means for sequentially positioning said apertures and said x-ray detectors in order to provide a plurality of overlapping x-ray beam paths between said single x-ray source and said conversion surface of said x-ray detectors, each of said overlapping beam paths extending radially from said single x-ray source, through said aperture, through a portion of said breast and through said conversion surface, and each of said overlapping beam paths defining a corresponding overlapping breast region,
g) a data acquisition means for acquiring digital image data from said detector array for each of said overlapping breast regions, said image data for each of said overlapping breast regions defining an image pane,
h) a computer programmed with a stitching algorithm for stitching together said image panes to create a composite x-ray image of at least a portion of said breast, the programmed computer performing the functions of:
  (1) registering each image pane onto a common pattern such that a portion of each image pane overlaps a portion of at least one other image pane,
  (2) blending overlapped portions of said image panes to create the composite x-ray image of at least a portion of said breast.

* * * * *